US007654998B1

(12) United States Patent
Ingenito

(10) Patent No.: US 7,654,998 B1
(45) Date of Patent: *Feb. 2, 2010

(54) TISSUE VOLUME REDUCTION

(75) Inventor: Edward Ingenito, Kingston, MA (US)

(73) Assignee: Aeris Therapeutics, Inc., Woburn, MA (US)

( * ) Notice: Subject to any disclaimer, the term of this patent is extended or adjusted under 35 U.S.C. 154(b) by 371 days.

This patent is subject to a terminal disclaimer.

(21) Appl. No.: 10/069,307

(22) PCT Filed: Aug. 23, 2000

(86) PCT No.: PCT/US00/23134

§ 371 (c)(1),
(2), (4) Date: Sep. 26, 2002

(87) PCT Pub. No.: WO01/13908

PCT Pub. Date: Mar. 1, 2001

Related U.S. Application Data

(63) Continuation-in-part of application No. 09/379,460, filed on Aug. 23, 1999, now Pat. No. 6,610,043.

(51) Int. Cl.
*A61M 31/00* (2006.01)

(52) U.S. Cl. ........................................ 604/514; 128/898

(58) Field of Classification Search ................... 604/19, 604/48, 500, 514, 93.01, 28, 35, 518, 522, 604/43.516, 102.01, 102.02, 101.01, 101.04, 604/79; 128/898, 207.15, 207.14; 514/802; 530/381, 382

See application file for complete search history.

(56) References Cited

U.S. PATENT DOCUMENTS

| | | | |
|---|---|---|---|
| 3,089,815 | A | 5/1963 | Lieb et al. |
| 4,013,507 | A | 3/1977 | Rembaum |
| 4,393,041 | A | 7/1983 | Brown et al. |
| 4,442,655 | A | 4/1984 | Stroetmann |
| 4,619,913 | A | 10/1986 | Luck |
| 4,631,055 | A | 12/1986 | Redl et al. |
| 4,719,282 | A | 1/1988 | Nadolsky et al. |
| 4,886,496 | A | 12/1989 | Conoscenti et al. |
| 4,973,582 | A | 11/1990 | Yoshida et al. |
| 5,290,552 | A | 3/1994 | Sierra et al. |

(Continued)

FOREIGN PATENT DOCUMENTS

| | | |
|---|---|---|
| EP | 0 303 756 | 2/1989 |

(Continued)

OTHER PUBLICATIONS

Cooper et al., "Bilateral pneumectomy (volume reduction) for chronic obstructive pulmonary disease", *J. Thorac. Cardiovasc. Surg.*, vol. 109, pp. 106-116, 1995.

(Continued)

*Primary Examiner*—Nicholas D Lucchesi
*Assistant Examiner*—Quynh-Nhu H Vu
(74) *Attorney, Agent, or Firm*—Dana M. Gordon; Foley Hoag LLP

(57) ABSTRACT

Devices, compositions, and methods for achieving non-surgical lung volume reduction (e.g., bronchoscopic lung volume reduction (BLVR)) are described. BLVR can be carried out by collapsing a region of the lung, adhering one portion of the collapsed region to another, and promoting fibrosis in or around the adherent tissue.

36 Claims, 16 Drawing Sheets

U.S. PATENT DOCUMENTS

| | | | | |
|---|---|---|---|---|
| 5,423,312 | A | 6/1995 | Siegmund et al. | |
| 5,437,292 | A | 8/1995 | Kipshidze et al. | |
| 5,583,114 | A | 12/1996 | Barrows et al. | |
| 5,651,982 | A | 7/1997 | Marx | |
| 5,660,175 | A | 8/1997 | Dayal | |
| 5,690,675 | A | 11/1997 | Sawyer et al. | |
| 5,714,470 | A | 2/1998 | Peet et al. | |
| 5,728,132 | A | 3/1998 | Van Tassel et al. | |
| 5,728,751 | A | 3/1998 | Patnaik | |
| 5,733,545 | A | 3/1998 | Hood, III | |
| 5,739,288 | A * | 4/1998 | Edwardson et al. | 530/382 |
| 5,773,418 | A | 6/1998 | Edwardson et al. | |
| 5,780,440 | A | 7/1998 | Lezdey et al. | |
| 5,782,748 | A | 7/1998 | Palmer et al. | |
| 5,814,022 | A * | 9/1998 | Antanavich et al. | 604/191 |
| 5,836,905 | A | 11/1998 | Lemelson et al. | |
| 5,883,084 | A | 3/1999 | Peterson et al. | |
| 5,980,866 | A | 11/1999 | Uchida et al. | |
| 6,001,814 | A | 12/1999 | Gyorkos et al. | |
| 6,117,425 | A | 9/2000 | MacPhee et al. | |
| 6,123,663 | A | 9/2000 | Rebuffat et al. | |
| 6,174,323 | B1 * | 1/2001 | Biggs et al. | 606/232 |
| 6,258,100 | B1 | 7/2001 | Alferness et al. | |
| 6,287,290 | B1 * | 9/2001 | Perkins et al. | 604/516 |
| 6,293,951 | B1 | 9/2001 | Alferness et al. | |
| 6,333,194 | B1 | 12/2001 | Levy et al. | |
| 6,592,594 | B2 | 7/2003 | Rimbaugh et al. | |
| 6,599,311 | B1 | 7/2003 | Biggs et al. | |
| 6,610,043 | B1 * | 8/2003 | Ingenito | 604/514 |
| 6,645,205 | B2 | 11/2003 | Ginn | |
| 6,682,520 | B2 * | 1/2004 | Ingenito | 604/514 |
| 6,723,302 | B1 * | 4/2004 | Clark et al. | 424/9.1 |
| 6,837,906 | B2 | 1/2005 | Ginn | |
| 6,878,141 | B1 | 4/2005 | Perkins et al. | |
| 6,886,558 | B2 | 5/2005 | Tanaka | |
| 6,929,637 | B2 | 8/2005 | Gonzalez et al. | |
| 2003/0099601 | A1 | 5/2003 | Gordon et al. | |
| 2003/0114384 | A1 | 6/2003 | Podolsky | |
| 2003/0134810 | A1 | 7/2003 | Springate et al. | |
| 2003/0181356 | A1 | 9/2003 | Ingenito | |
| 2004/0038868 | A1 | 2/2004 | Ingenito | |
| 2004/0047855 | A1 | 3/2004 | Ingenito | |
| 2005/0130176 | A1 | 6/2005 | Vogelstein et al. | |

FOREIGN PATENT DOCUMENTS

| | | |
|---|---|---|
| EP | 0627266 | 12/1994 |
| EP | 1206276 | 5/2002 |
| RU | 2092108 | 10/1997 |
| RU | 2130946 | 5/1999 |
| WO | WO-9209301 | 6/1992 |
| WO | WO-9213547 | 8/1992 |
| WO | WO-9407607 | 4/1994 |
| WO | WO 95/13748 | 5/1995 |
| WO | WO-9613292 | 5/1996 |
| WO | WO-9616983 | 6/1996 |
| WO | WO-9729851 | 8/1997 |
| WO | WO 99/25782 | 5/1999 |
| WO | WO 01/02042 | 1/2001 |
| WO | WO-0113908 | 3/2001 |
| WO | WO-0126721 | 4/2001 |
| WO | WO-03105676 | 12/2003 |

OTHER PUBLICATIONS

Cooper et al., "Results of 150 consecutive bilateral lung volume reduction procedures in patients with severe emphysema", *J. Thorac. Cardiovasc. Surg.*, vol. 112, pp. 1319-1329, 1996.

Enhorning, "Pulsating bubble technique for evaluating pulmonary surfactant", *J. Appl. Physiol.*, vol. 43, pp. 198-203, 1977.

Florkiewicz et al., "Human basic fibroblast growth factor gene encodes four polypeptides: three initiate translation from non-AUG codons", *Proc. Natl. Acad. Sci. USA*, vol. 86, pp. 3978-3981, 1999.

Gibson et al., "Exponential description of the static pressure-volume curve of normal and diseased lungs", *Am. Rev. Resp. Dis.*, vol. 120, pp. 799-811, 1979.

Hoppin, "Theoretical basis for improvement following reduction pneumoplasty in emphysema", *Am. J. Resp. Crit. Care Med.*, vol. 155, pp. 520-525, 1997.

Kotloff et al., "Bilateral lung volume reduction surgery for advanced emphysema: A companion of median stemotomy and thorascopic approaches", *Chest*, vol. 110, pp. 1399-1406, 1996.

Kennedy et al., "Mechanisms of surfactant dysfunction in early acute lung injury", *Exp. Lung Res.*, vol. 23, pp. 171-189, 1997.

Lutchen et al., "Optimal ventilation waveforms for estimating low-frequency respiratory impedance", *J. Appl. Physiol.*, vol. 75, pp. 478-488, 1993.

Martinez et al., "Lung-volume reduction improves dyspnea, dynamic hyperinflation, and respiratory muscle function", *Am. J. Resp. Crit. Care Med.*, vol. 155, pp. 1984-1990, 1997.

Silberstein et al., "An autologous fibrinogen-based adhesive for use in otologic surgery", *Transfusion*, vol. 28, pp. 319-321, 1988.

Stamenovic, "Micromechanical foundations of pulmonary elasticity", *Physiol. Rev.*, vol. 70, pp. 1117-1134, 1990.

Suki et al., "Relationship between frequency and amplitude dependence in the lung: a nonlinear block-structured modeling approach", *J. Appl. Physiol.*, vol. 79, No. 2, pp. 660-671, 1995.

Swanson et al., "No-cut thoracoscopic lung plication: a new technique for lung volume reduction surgery", *J. Am. Coll. Surg.*, vol. 185, pp. 25-32, 1997.

Bergeron, M. et al., "Pharmacodynamics of antibiotics in fibrin clots", Journal of Antimicrobial Chemotherapy (1993) 31, Suppl. D, 113-136.

[No Author Listed] Surfactant replacement therapy for respiratory distress syndrome. American Academy of Pediatrics. Committee on Fetus and Newborn. Pediatrics. Mar. 1999;103(3):684-5.

[No Author Listed] Continuous or nocturnal oxygen therapy in hypoxemic chronic obstructive lung disease: a clinical trial. Nocturnal Oxygen Therapy Trial Group. Ann Intern Med. Sep. 1980;93(3):391-8.

Baumann et al., Closure of a bronchopleural fistula using decalcified human spongiosa and a fibrin sealant. Ann Thorac Surg. Jul. 1997:64(1):230-3.

Berlin et al., Are porphyrin mixtures favorable photodynamic anticancer drugs? A model study with combinatorial libraries of tetraphenylporphyrins. Comb Chem. 1998;61:107-8.

Camilli et al., Longitudinal changes in forced expiratory volume in one second in adults. Effects of smoking and smoking cessation. Am Rev Respir Dis. Apr. 1987;135(4):794-9.

Carr et al., Effect of homo poly(L-amino acids) on fibrin assembly: role of charge and molecular weight. Biochemistry, vol. 28, No. 3 (1989) 1388-1395.

Carr et al., Effect of glycosaminoglycans on Thrombin- and atroxin-induced fibrin assembly and structure. 62(4) 1057-1061 (1989).

Coyle et al., Human eosinophil-granule major basic protein and synthetic polycations induce airway hyperresponsiveness in vivo dependent on bradykinin generation. J Clin Invest. Apr. 1995;95(4):1735-40.

Dallas et al., Measuring interactions between ECM and TGFβ-like proteins. Chapter 19: Methods in Molecular Biology. 2000;139:231-43.

Daniel et al., Lung volume reduction surgery. Case selection, operative technique, and clinical results. Ann Surg. May 1996;223(5):526-31; discussion 532-3.

Deyerling et al., A suspension of fibrin glue and antibiotic for local treatment of mycotic aneurysms in endocarditis—an experimental study. Thorac Cardiovasc Surg. Dec. 1984;32(6):369-72.

Drummond et al., Optimizing liposomes for delivery of chemotherapeutic agents to solid tumors. Pharmacol Rev. Dec. 1999;51(4):691-743.

Fessler et al., Lung volume reduction surgery and airflow limitation. Am J Respir Crit Care Mar. 1998;157(3 Pt 1):715-22.

Fok et al., Randomised controlled study of early use of inhaled corticosteroid in preterm infants with respiratory distress syndrome. Arch Dis Child Fetal Neonatal Ed. May 1999;80(3):F203-8.

Gelb et al., Lung function 5 yr after lung volume reduction surgery for emphysema. Am J Respir Crit Care Med. Jun. 2001;163(7):1562-6.

Gilman et al., The role of the carbohydrate moiety in the biologic properties of fibrinogen. J Biol Chem. Mar. 10, 1984;259(5):3248-53.

Golab et al., Potentiation of the anti-tumour effects of Photofrin-based photodynamic therapy by localized treatment with G-CSF. Br J Cancer. Apr. 2000;82(8):1485-91.

Grishakov et al., Temporary endobronchial occlusion in a complex treatment of purulent-destructive lesions of the lungs and pleura. Synopsis of the Candidate of Sciences degree thesis. 1988. Russian.

Gustafsson et al., The 21-residue surfactant peptide (LysLeu4)4Lys(KL4) is a transmembrane alpha-helix with a mixed nonpolar/polar surface. FEBS Lett. Apr. 15, 1996;384(2):185-8.

Hantos et al., Mechanical impedances of lungs and chest wall in the cat. J Appl Physiol. Aug. 1992;73(2):427-33.

Hautamaki et al., Requirement for macrophage elastase for cigarette smoke-induced emphysema in mice. Science. Sep. 26, 1997;277(5334):2002-4.

Hürter et al., Endobronchial sonography: feasibility and preliminary results. Thorax. Jul. 1992;47(7):565-7.

Ingenito et al., Biophysical characterization and modeling of lung surfactant components. J Appl Physiol. May 1999;86(5):1702-14.

Ingenito et al., Pivotal role of anionic phospholipids in determining dynamic behavior of lung surfactant. Am J Respir Crit Care Med. Mar. 2000;161(3 Pt 1):831-8.

Ingenito et al., Comparison of physiological and radiological screening for lung volume reduction surgery. Am J Respir Crit Care Med. Apr. 2001;163(5):1068-73.

Ingenito et al., Interpreting improvement in expiratory flows after lung volume reduction surgery in terms of flow limitation theory. Am J Respir Crit Care Med. Apr. 2001;163(5):1074-80.

Ingenito et al., Bronchoscopic volume reduction: a safe and effective alternative to surgical therapy for emphysema. Am J Respir Crit Care Med. Jul. 15, 2001;164(2):295-301.

Innis et al., Evolutionary trace analysis of TGF-beta and related growth factors: implications for site-directed mutagenesis. Protein Eng. Dec. 2000;13(12):839-47.

Itoh et al., [A fibrin clot containing of anticancer drug for intra-arterial chemo-embolization therapy. (1) Experimental study on basic characteristics in dogs] Gan To Kagaku Ryoho. Feb. 1985;12(2):250-7. Japanese.

König et al., Pdt of tumor-bearing mice using liposome delivered texaphyrins. International Conference, Milan, Italy. Jun. 24-27, 1992.

Kononov et al., Roles of mechanical forces and collagen failure in the development of elastase-induced emphysema. Am J Respir Crit Care Med. Nov. 15, 2001;164(10 Pt 1):1920-6.

Kreimer-Birnbaum et al., Modified porphyrins, chlorins, phthalocyanines, and purpurins: second-generation photosensitizers for photodynamic therapy. Semin Hematol. Apr. 1989;26(2):157-73.

Kusanagi et al., Characterization of a bone morphogenetic protein-responsive Smad-binding element. Mol Biol Cell. Feb. 2000;11(2):555-65.

Lalvani et al., Rapid detection of Mycobacterium tuberculosis infection by enumeration of antigen-specific T cells. Am J Respir Crit Care Med. Mar. 2001;163(4):824-8.

Leboeuf, et al. Effects of hyaluronic acid and other glycosaminoglycans on fibrin polymer formation. Biochemistry 1987, 26 6052-6057.

Lin et al., Induction of pulmonary fibrosis in organ-cultured rat lung by cadmium chloride and transforming growth factor-beta1. Toxicology. May 15, 1998;127(1-3):157-66.

Lipp et al., Phase and morphology changes in lipid monolayers induced by SP-B protein and its amino-terminal peptide. Science. Aug. 30, 1996;273(5279):1196-9.

McKenna et al., Should lung volume reduction for emphysema be unilateral or bilateral? J Thorac Cardiovasc Surg. Nov. 1996;112(5):1331-8; discussion 1338-9.

McLean et al., An amphipathic alpha-helical decapeptide in phosphatidylcholine is an effective synthetic lung surfactant. Am Rev Respir Dis. Feb. 1993;147(2):462-5.

Ney et al., Fibrin glue-antibiotic suspension in the prevention of prosthetic graft infection. J Trauma. Aug. 1990;30(8):1000-5; discussion 1005-6.

Nilsson et al., Synthetic peptide-containing surfactants—evaluation of transmembrane versus amphipathic helices and surfactant protein C poly-valyl to poly-leucyl substitution. Eur J Biochem. Jul. 1, 1998;255(1):116-24.

Otis et al., Dynamic surface tension of surfactant TA: experiments and theory. J Appl Physiol. Dec. 1994;77(6):2681-8.

Pass et al., Photodynamic therapy in oncology: mechanisms and clinical use. J Natl Cancer Inst. Mar. 17, 1993;85(6):443-56.

Richert et al., A long-time-stable liposome formulation for porphyrinoid photosensitizers. J Photochem Photobiol B: Biol. 1993;19:67-73.

Shapiro et al., The macrophage in chronic obstructive pulmonary disease. Am J Respir Crit Care Med. Nov. 1999:160(5 Pt 2):S29-32.

Sime et al., Adenovector-mediated gene transfer of active transforming growth factor-beta1 induces prolonged severe fibrosis in rat lung. J Clin Invest. Aug. 15, 1997;100(4):768-76.

Smith et al., Activity of two polyene and two imidazole antimicrobics on Candida albicans in human fibrin clots. J Lab Clin Med. Jul. 1983:102(1):126-32.

Sugitachi et al., Japan J Cancer Chemother 16(8)2814-2817 Aug. 1989. (Abstract).

Suki et al., On the progressive nature of emphysema: roles of proteases, inflammation and mechanical forces. Am. J. of Resp. and Critical Care Med. vol. 168 516-521 (2003).

Varoli et al., Endoscopic treatment of bronchopleural fistulas. Ann Thorac Surg. Mar. 1998;65(3):807-9.

Whitman et al., TGF-beta superfamily signaling and left-right asymmetry. Sci STKE. Jan. 9, 2001;2001(64):RE1.

Yanagisawa. et al., [Endoscopic closure of the postoperative bronchopleural fistula] Kyobu Geka. Oct. 1992;45(11):975-8. Japanese.

Ziesche et al., A preliminary study of long-term treatment with interferon gamma-1b and low-dose prednisolone in patients with idiopathic pulmonary fibrosis. N Engl J Med. Oct. 21, 1999;341(17):1264-9. Erratum in: N Engl J Med Feb. 17, 2000;342(7):524.

* cited by examiner b* vs Pr/PL for fibrinogen b* vs Pr/PL for albumin

Figure 8a
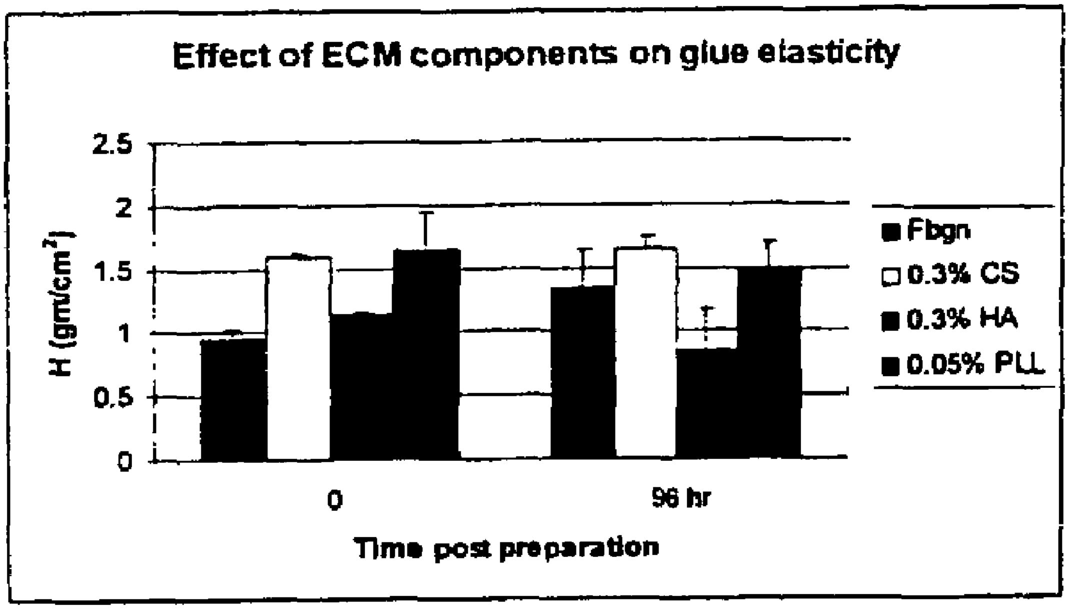
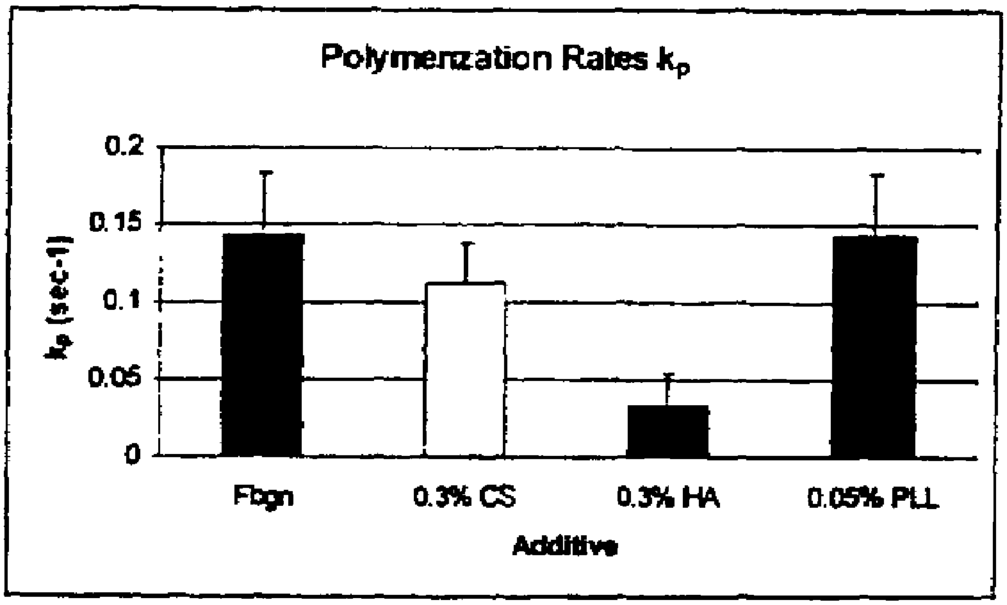
Figure 8b 100
110a
112
102a
105
105b
102a
102
105a
111
101
A
110
101a
101b
101
108
107

TISSUE VOLUME REDUCTION

This application is a national stage filing under 35 U.S.C. §371 of PCT International Application PCT/US00/23134 filed Aug. 23, 2000 which claims priority to, and is a continuation-in-part of, U.S. patent application Ser. No. 09/379,460 filed on Aug. 23, 1999, now issued as U.S. Pat. No. 6,610,043, the disclosures of each of which are incorporated herein in their entirety.

BACKGROUND OF THE INVENTION

The field of the invention is tissue repair and volume reduction, for example, lung repair and volume reduction.

End stage emphysema can be treated with lung volume reduction surgery (LVRS) (see, e.g., Cooper et al., *J. Thorac. Cardiovasc. Surg.* 109:106-116, 1995). While it may seem counter-intuitive that respiratory function would be improved by removing part of the lung, excising over-distended tissue (as seen in patients with heterogeneous emphysema) allows adjacent regions of the lung that are more normal to expand. In turn, this expansion allows for improved recoil and gas exchange. Even patients with homogeneous emphysema benefit from LVRS because resection of abnormal lung results in overall reduction in lung volumes, an increase in elastic recoil pressures, and a shift in the static compliance curve towards normal (Hoppin, *Am. J. Resp. Crit. Care Med.* 155:520-525, 1997).

While many patients who have undergone LVRS experience significant improvement (Cooper et al., *J. Thorac. Cardiovasc. Surg.* 112:1319-1329, 1996), they have assumed substantial risk. LVRS is carried out by surgically removing a portion of the diseased lung, which has been accessed either by inserting a thoracoscope through the chest wall or by a more radical incision along the sternum (Katloff et al., *Chest* 110:1399-1406, 1996). Thus, gaining access to the lung is traumatic. and the subsequent procedures, which can include stapling the fragile lung tissue, can cause serious post-operative complications.

SUMMARY OF THE INVENTION

The invention features devices, compositions, and methods for repairing tissue and for achieving non-surgical tissue (e.g., lung) volume reduction. In one aspect, the methods are carried out on lung tissue using a bronchoscope. This method completely eliminates the need for surgery because it allows the tissue reduction procedure to be performed through the patient's trachea and smaller airways. In this approach, bronchoscopic lung volume reduction (BLVR) is performed by collapsing a region of the lung, adhering one portion of the collapsed region to another, and promoting fibrosis in or around the adherent tissue. The composition used to achieve lung collapse may be, but is not necessarily, the same as that used to form adhesions within the tissue. Preferred embodiments may include one or more of the following features.

There are numerous ways to induce lung collapse. For example, a material that increases the surface tension of fluids lining the alveoli (i.e., a material that can act as an anti-surfactant) can be introduced through the bronchoscope (preferably, through a catheter lying within the bronchoscope). The material can include fibrinogen, fibrin, or biologically active fragments thereof. Lung collapse can also be induced by blocking air flow into and out of the region of the lung that is targeted for collapse. This is achieved by inserting a balloon catheter through the bronchoscope and inflating the balloon so that it occludes the bronchus or bronchiole into which it has been placed. Prior to inducing lung collapse, the lung can be filled with oxygen so that retained gas can be absorbed into the blood.

Similarly, there are numerous ways to promote adhesion between one portion of the collapsed lung and another. If fibrinogen is selected as the anti-surfactant, adhesion is promoted by exposing the fibrinogen to a fibrinogen activator, such as thrombin, which cleaves fibrinogen and polymerizes the resulting fibrin. Other substances, including thrombin receptor agonists and batroxobin, can also be used to activate fibrinogen. If fibrin is selected as the anti-surfactant, no additional substance or compound need be administered; fibrin can polymerize spontaneously, thereby adhering one portion of the collapsed tissue to another.

Fibrosis is promoted by providing one or more polypeptide growth factors together with one or more of the anti-surfactant or activator substances described above. The growth factors can be selected from the fibroblast growth factor (FGF) family or can be transforming growth factor beta-like (TGFβ-like) polypeptides.

The compositions described above can also contain one or more antibiotics to help prevent infection. Alternatively, or in addition, antibiotics can be administered via other routes (e.g., they may be administered orally or intramuscularly).

Other aspects of the invention include the compositions described above for promoting collapse and/or adhesion, as well as devices for introducing the composition into the body. For example, in one aspect, the invention features physiologically acceptable compositions that include a polypeptide growth factor or a biologically active fragment thereof (e.g., a platelet-derived growth factor, a fibroblast growth factor (FGF), or a transforming growth factor-β-like polypeptide) and fibrinogen, or a fibrin monomer (e.g., a fibrin I monomer, a fibrin II monomer, a des BB fibrin monomer, or any mixture or combination thereof), or a fibrinogen activator (e.g., thrombin). The fibrinogen, fibrin monomers, and fibrinogen activators useful in BLVR can be biologically active mutants (e.g., fragments) of these polypeptides.

In another aspect, the invention features devices for performing non-surgical lung volume reduction. For example, the invention features a device that includes a bronchoscope having a working channel and a catheter that can be inserted into the working channel. The catheter can contain multiple lumens and can include an inflatable balloon. Another device for performing lung volume reduction includes a catheter having a plurality of lumens (e.g., two or more) and a container for material having a plurality of chambers (e.g., two or more), the chambers of the container being connectable to the lumens of the catheter. These devices can also include an injector to facilitate movement of material from the container to the catheter.

BLVR has several advantages over standard surgical lung volume reduction (LVRS). BLVR should reduce the morbidity and mortality known to be associated with LVRS (Swanson et al., *J. Am. Coll. Surg.* 185:25-32, 1997). Atrial arrhythmias and prolonged air leaks, which are the most commonly reported complications of LVRS, are less likely to occur with BLVR because BLVR does not require stapling of fragile lung tissue or surgical manipulations that irritate the pericardium. BLVR may also be considerably less expensive than SLVR, which currently costs between approximately $18,000 and $26,000 per case. The savings would be substantial, given that emphysema afflicts between two and six million patients in America alone. In addition, some patients who would not be candidates for LVRS (due, e.g., to their advanced age) may undergo BLVR. Moreover, should the need arise, BLVR affords patients an opportunity to undergo more than one volume reduction procedure. While repeat surgical intervention is not a viable option for most patients (because of pleural adhesions that form following the original procedure), no such limitation should exist for patients who have undergone BLVR.

Other features and advantages of the invention will be apparent from the following detailed description, and from the claims.

BRIEF DESCRIPTION OF THE DRAWINGS

FIGS. 8*a* and 8*b* are bar graphs summarizing elastic moduli of gel strips containing various ECM components (FIG. 8*a*) and gel polymerization rates (FIG. 8*b*).

DETAILED DESCRIPTION

Figure 1:
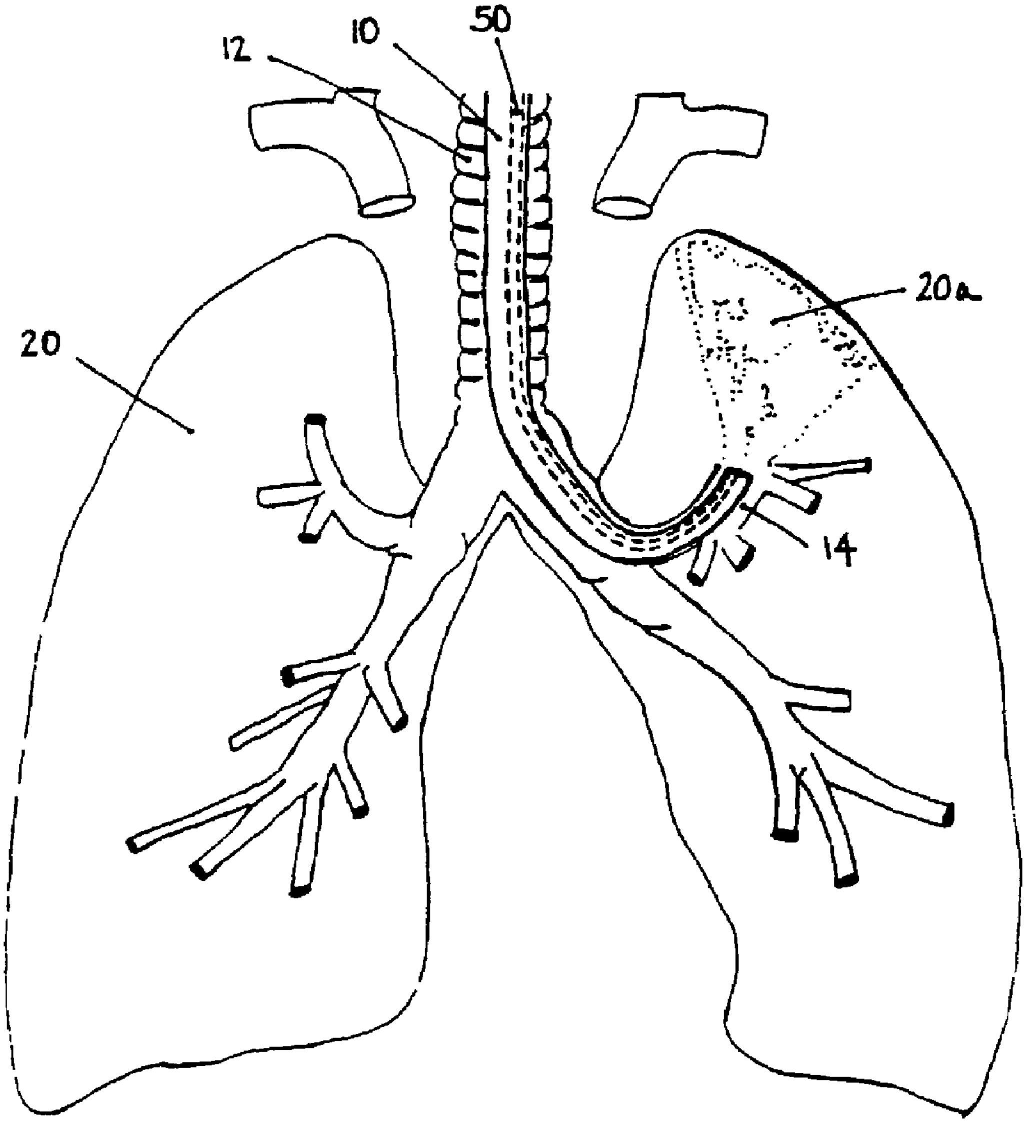
FIG. 1 is a schematic representation of BLVR.

The devices, compositions, and methods described herein can be used to repair injuries to or leaks in tissues such as the lung, which can be caused by trauma, disease, or surgical procedures, as well as to reduce the volume of inherently collapsible tissue. For example, lung volume can be reduced using a bronchoscope (bronchoscopic lung volume reduction is abbreviated herein as BLVR). Referring to FIG. 1, a flexible bronchoscope 10 is inserted through a patient's trachea 12 to a target region 20*a* of the lung 20, and a balloon catheter 50 with a distal lumen port 60 (FIG. 2) is inserted through a channel within the bronchoscope. Target region 20*a* will collapse either when the air passage 14 to target region 20*a* is occluded or when an anti-surfactant is administered through balloon catheter 50 to target region 20*a*. Regardless of the cause of collapse, one portion of the collapsed target region will adhere to another when exposed to one or more of the compositions described below. These compositions include substances that can polymerize either spontaneously (e.g., fibrin) or in response to an activator (e.g., fibrinogen). In addition, one or more of the compositions contains a polypeptide growth factor that promotes fibrosis, and may contain an antibiotic to help prevent infection or an additional factor (such as factor XIIIa transglutaminase) to promote polymerization. Following application of the composition(s), the bronchoscope is removed.

Patients who have chronic obstructive pulmonary disease can benefit from BLVR. These patients include, but are not limited to, those who have emphysema, chronic asthma, chronic bronchitis, and brochiectasis. BLVR can also be performed when a patient's lung is damaged by trauma or in the event of a spontaneous pneumothorax. While the compositions of the invention (which may be referred to herein variously as solutions, glues, and gels) can be applied with novel devices of the present invention, they can also be applied independently. For example, the compositions can be applied during surgical LVR or during any surgical procedure that places a patient at risk of experiencing damage to the lung, other tissues within the respiratory tract, other organs, or other organ systems. Some of the uses for the compositions of the invention are described more specifically under the heading, "Other Embodiments."

Identifying and Gaining Access to a Target Region of the Lung

Once a patient is determined to be a candidate for BLVR, the target region 20*a* of the lung can be identified using radiological studies (e.g., chest X-rays) and computed tomography scans. When the procedure is subsequently performed, the patient is anesthetized and intubated, and can be placed on an absorbable gas (e.g., at least 90% oxygen and up to 100% oxygen) for a specified period of time (e.g., approximately 30 minutes). The region(s) of the lung that were first identified radiologically are then identified bronchoscopically.

Suitable bronchoscopes include those manufactured by Pentax, Olympus, and Fujinon, which allow for visualization of an illuminated field. The physician guides bronchoscope 10 into trachea 12 and through the bronchial tree so that the open tip 60 of bronchoscope 10 is positioned at the entrance to target region 20*a* (i.e., to the region of the lung that will be reduced in volume). Bronchoscope 10 can be guided through progressively narrower branches of the bronchial tree to reach various subsegments of either lung 20. For example, as shown in FIG. 1, the bronchoscope can be guided to a subsegment within the upper lobe of the patient's left lung.

The balloon catheter 50 mentioned above (and described more fully below) is then guided through bronchoscope 10 to target region 20*a* of lung 20. When catheter 50 is positioned within bronchoscope 10, balloon 58 is inflated so that material passed through the catheter will be contained in regions of the lung distal to the balloon. The targeted region can be lavaged with saline to reduce the amount of surfactant that is naturally present, and a physiologically compatible composition containing an anti-surfactant (i.e., an agent that increases the surface tension of fluids lining the alveoli) is applied to the targeted region of the lung through the catheter. Preferably, the composition is formulated as a solution or suspension and includes fibrin or fibrinogen. An advantage of administering these substances is that they can each act not only as anti-surfactants, but can participate in the adhesive process as well.

Fibrinogen-Based Solutions

Fibrinogen can function as an anti-surfactant because it increases the surface tension of fluids lining the alveoli, and it can function as a sealant or adhesive because it can participate in a coagulation cascade in which it is converted to a fibrin monomer that is then polymerized and cross-linked to form a stable mesh. Fibrinogen, which has also been called Factor I, represents about 2-4 g/L of blood plasma protein, and is a monomer that consists of three pairs of disulfide-linked polypeptide chains designated $(A\alpha)_2$, $(B\beta)_2$, and $\gamma_2$. The "A" and "B" chains represent the two small N-terminal peptides and are also known as fibrinopeptides A and B, respectively. The cleavage of fibrinogen by thrombin results in a compound termed fibrin I, and the subsequent cleavage of fibrinopeptide B results in fibrin IL Although these cleavages reduce the molecular weight of fibrinogen only slightly, they nevertheless expose the polymerization sites. In the process of normal clot formation, the cascade is initiated when fibrinogen is exposed to thrombin, and this process can be replicated in the context of lung volume reduction when fibrinogen is exposed to an activator such as thrombin, or an agonist of the thrombin receptor, in an aqueous solution containing calcium (e.g. 1.5 to 5.0 mM calcium).

The fibrinogen-containing composition can include 3-12% fibrinogen and, preferably, includes approximately 10% fibrinogen in saline (e.g., 0.9% saline) or another physiologically acceptable aqueous solution. The volume of anti-surfactant administered will vary, depending on the size of the region of the lung, as estimated from review of computed tomagraphy scanning of the chest. For example, the targeted region can be lavaged with 10-100 mls (e.g., 50 mls) of fibrinogen solution (10 mg/ml). To facilitate lung collapse, the target region can be exposed to (e.g., rinsed or lavaged with) an unpolymerized solution of fibrinogen and then exposed to a second fibrinogen solution that is subsequently polymerized with a fibrinogen activator (e.g., thrombin or a thrombin receptor agonist).

The anti-surfactant can contain fibrinogen that was obtained from the patient before the non-surgical lung reduction procedure commenced (i.e., the anti-surfactant or adhesive composition can include autologous fibrinogen). The use of an autologous substance is preferable because it eliminates the risk that the patient will contract some form of hepatitis (e.g., hepatitis B or non A, non B hepatitis), an acquired immune deficiency syndrome (AIDS), or other blood-transmitted infection. These infections are much more likely to be contracted when the fibrinogen component is extracted from pooled human plasma (see, e.g., Silberstein et al., *Transfusion* 28:319-321, 1988). Human fibrinogen is commercially available through suppliers known to those of skill in the art or may be obtained from blood banks or similar depositories.

Polymerization of fibrinogen-based anti-surfactants can be achieved by adding a fibrinogen activator. These activators are known in the art and include thrombin, batroxobin (such as that from *B. Moojeni, B. Maranhao, B. atrox, B. Ancrod*, or *A. rhodostoma*), and thrombin receptor agonists. When combined, fibrinogen and fibrinogen activators react in a manner similar to the final stages of the natural blood clotting process to form a fibrin matrix. More specifically, polymerization can be achieved by addition of thrombin (e.g., 1-10 units of thrombin per ng of fibrinogen). If desired, 1-5% (e.g., 3%) factor XIIIa transglutaminase can be added to promote cross-linking.

In addition, to promote fibrosis (or scarring) at the site where one region of the collapsed lung adheres to another, one or more of the compositions applied to achieve lung volume reduction (e.g., the composition containing fibrinogen) can contain a polypeptide growth factor. Numerous factors can be included. Platelet-derived growth factor (PDGF) and those in the fibroblast growth factor and transforming growth factor-β families are preferred.

For example, the polypeptide growth factor included in a composition administered to reduce lung volume (e.g., the fibrinogen-, fibrinogen activator-, or fibrin-based compositions described herein) can be basic FGF (bFGF), acidic FGF (aFGF), the hst/Kfgf gene product, FGF-5, FGF-10, or int-2. The nomenclature in the field of polypeptide growth factors is complex, primarily because many factors have been isolated independently by different researchers and, historically, named for the tissue type used as an assay during purification of the factor. This complexity is illustrated by basic FGF, which has been referred to by at least 23 different names (including leukemic growth factor, macrophage growth factor, embryonic kidney-derived angiogenesis factor 2, prostatic growth factor, astroglial growth factor 2, endothelial growth factor, tumor angiogenesis factor. hepatoma growth factor, chondrosarcoma growth factor, cartilage-derived growth factor 1, eye-derived growth factor 1, heparin-binding growth factors class II, myogenic growth factor, human placenta purified factor, uterine-derived growth factor, embryonic carcinoma-derived growth factor, human pituitary growth factor, pituitary-derived chondrocyte growth factor, adipocyte growth factor, prostatic osteoblastic factor, and mammary tumor-derived growth factor). Thus, any factor referred to by one of the aforementioned names is within the scope of the invention.

The compositions can also include "functional polypeptide growth factors," i.e., growth factors that, despite the presence of a mutation (be it a substitution, deletion, or addition of amino acid residues) retain the ability to promote fibrosis in the context of lung volume reduction. Accordingly, alternate molecular forms of polypeptide growth factors (such as the forms of bFGF having molecular weights of 17.8, 22.5, 23.1, and 24.2 kDa) are within the scope of the invention (the higher molecular weight forms being colinear N-terminal extensions of the 17.8 kDa bFGF (Florkiewicz et al., *Proc. Natl. Acad. Sci. USA* 86:3978-3981, 1989)).

It is well within the abilities of one of ordinary skill in the art to determine whether a polypeptide growth factor, regardless of mutations that affect its amino acid content or size, substantially retains the ability to promote fibrosis as would the full length, wild type polypeptide growth factor (i.e., whether a mutant polypeptide promotes fibrosis at least 40%, preferably at least 50%, more preferably at least 70%, and most preferably at least 90% as effectively as the corresponding wild type growth factor). For example, one could examine collagen deposition in cultured fibroblasts following exposure to full-length growth factors and mutant growth factors. A mutant growth factor substantially retains the ability to promote fibrosis when it promotes at least 40%, preferably at least 50%, more preferably at least 70%, and most preferably at least 90% as much collagen deposition as does the corresponding, wild-type factor. The amount of collagen deposition can be measured in numerous ways. For example, collagen expression can be determined by an immunoassay.

Alternatively, collagen expression can be determined by extracting collagen from fibroblasts (e.g., cultured fibroblasts or those in the vicinity of the reduced lung tissue) and measuring hydroxyproline.

The polypeptide growth factors useful in the invention can be naturally occurring, synthetic, or recombinant molecules and can consist of a hybrid or chimeric polypeptide with one portion, for example, being bFGF or TGFβ, and a second portion being a distinct polypeptide. These factors can be purified from a biological sample, chemically synthesized, or produced recombinantly by standard techniques (see, e.g., Ausubel et al., *Current Protocols in Molecular Biology*, New York, John Wiley and Sons, 1993; Pouwels et al., *Cloning Vectors: A Laboratory Manual,* 1985, Supp. 1987).

Of course, various fibrosis-promoting growth factors can be used in combination.

One of ordinary skill in the art is well able to determine the dosage of a polypeptide growth factor required to promote fibrosis in the context of BLVR. The dosage required can vary and can range from 1-100 nM.

In addition, any of the compositions or solutions described herein for lung volume reduction (e.g., the fibrinogen-based composition described above) can contain one or more antibiotics (e.g., ampicillin, gentamycin, cefotaxim, nebacetin, penicillin, or sisomicin). The inclusion of antibiotics in therapeutically applied compositions is well known to those of ordinary skill in the art.

Fibrin-Based Solutions

Fibrin can also function as an anti-surfactant as well as a sealant or adhesive. However, in contrast to fibrinogen, fibrin can be converted to a polymer without the application of an activator (such as thrombin or factor XIIIa). In fact, fibrin I monomers can spontaneously form a fibrin I polymer that acts as a clot, regardless of whether they are crosslinked and regardless of whether fibrin I is further converted to fibrin II polymer. Without limiting the invention to compounds that function by any particular mechanism, it can be noted that when fibrin I monomers come into contact with a patient's blood, the patient's own thrombin and factor XIII may convert the fibrin I polymer to crosslinked fibrin II polymer.

Any form of fibrin monomer that can be converted to a fibrin polymer can be formulated as a solution and used for lung volume reduction. For example, fibrin-based compositions can contain fibrin I monomers, fibrin II monomers, des BB fibrin monomers, or any mixture or combination thereof. Preferably, the fibrin monomers are not crosslinked.

Fibrin can be obtained from any source so long as it is obtained in a form that can be converted to a fibrin polymer (similarly, non-crosslinked fibrin can be obtained from any source so long as it can be converted to crosslinked fibrin). For example, fibrin can be obtained from the blood of a mammal, such as a human, and is preferably obtained from the patient to whom it will later be administered (i.e., the fibrin is autologous fibrin). Alternatively, fibrin can be obtained from cells that, in culture, secrete fibrinogen.

Fibrin-based compositions can be prepared as described in U.S. Pat. No. 5,739,288 (which is hereby incorporated by referenced in its entirety), and can contain fibrin monomers having a concentration of no less than about 10 mg/ml. For example, the fibrin monomers can be present at concentrations of from about 20 mg/ml to about 200 mg/ml; from about 20 mg/ml to about 100 mg/ml; and from about 25 mg/ml to about 50 mg/ml.

The spontaneous conversion of a fibrin monomer to a fibrin polymer can be facilitated by contacting the fibrin monomer with calcium ions (as found, e.g., in calcium chloride, e.g., a 3-30 mM $CaCl_2$ solution). Except for the first two steps in the intrinsic blood clotting pathway, calcium ions are required to promote the conversion of one coagulation factor to another. Thus, blood will not clot in the absence of calcium ions (but, in a living body, calcium ion concentrations never fall low enough to significantly affect the kinetics of blood clotting; a person would die of muscle tetany before calcium is diminished to that level). Calcium-containing solutions (e.g., sterile 10% $CaCl_2$) can be readily made or purchased from a commercial supplier.

The fibrin-based compositions described here can also include one or more polypeptide growth factors that promote fibrosis (or scarring) at the site where one region of the collapsed lung adheres to another. Numerous factors can be included and those in the fibroblast growth factor and transforming growth factor-β families are preferred. The polypeptide growth factors suitable for inclusion with fibrin-based compositions include all of those (described above) that are suitable for inclusion with fibrinogen-based compositions.

Solutions that Include Components of the Extracellular Matrix

As described herein, an effective way of achieving safe, non-surgical tissue volume reduction is to use solutions containing agents that act not only mechanically to adhere one portion of a tissue to another, but also biologically to modulate responses of the cells within the areas targeted for volume reduction. Thus, the fibrin- and fibrinogen-based solutions described above can also contain one or more agents that enhance the mechanical and biological properties of the solutions. As described above, such solutions can be used to lavage (i.e. to wash out) the tissue or to adhere one portion of the tissue to another.

Useful agents include those that: (1) promote fibroblast and mononuclear cell chemotaxis and collagen deposition in a self-limited and localized manner; (2) dampen the activity of alveolar epithelial cells, either by inhibiting their ability to express surfactant, which promotes reopening of target regions, or by promoting epithelial cell apoptosis, which causes inflammation; (3) promote epithelial cell constriction, which decreases blood flow to target regions, thereby minimizing mismatching between ventilation and perfusion and any resulting gas exchange abnormalities. More specifically, solutions containing components of the extracellular matrix (ECM), endothelin-1, and/or pro-apoptotic reagents can be used. Suitable pro-apoptotic agents include proteins in the Bcl-2 family (e.g., Bax, Bid, Bik, Bad, and Bim and biologically active fragments or variants thereof), proteins in the caspase family (e.g., caspase-3, caspase-8, caspase-9, and biologically active fragments or variants thereof), and proteins in the annexin family (e.g. annexin V, or a biologically active fragment or variant thereof). As described further in the Examples below, solutions containing several of these agents have been tested. The first agents to be tested were selected based on their biological attributes, their biophysical effects on gel behavior, their solubility in aqueous solutions (under physiological conditions), and cost. Those of ordinary skill in the art will be able to recognize and use comparable agents without resort to undue experimentation.

The agents selected for use initially were chondroitin sulfate A, low and high molecular weight hyaluronic acid, fibronectin, medium and long chain poly-L-lysine, and the collagen dipeptide proline-hydroxyproline.

Chondroitin sulfate (CS) is an ECM component of the glycosaminoglycan (GAG) family. It is a sulfated carbohydrate polymer composed of repeating dissacharide units of galactosamine linked to glucuronic acid via a beta 1-4 carbon linkage. CS is not found as a free carbohydrate moiety in vivo, but rather is bound to core proteins of various types. As such, it is a component of several important ECM proteoglycans including members of the syndecan family (syndecan 1-4), leucine-rich family (decortin, biglycan), and the hyaluronate binding family (CD44, aggrecan, versican, neuroncan). These CS-containing proteoglycans function in the binding of cell surface integrins and growth factors. CS-containing proteoglycans may function within the lung as scaffolding for collagen deposition by fibroblasts. Thus, ECM components within the glycosaminoglycan family, particularly carbohydrate polymers, are useful in achieving tissue volume reduction (e.g., lung volume reduction carried out bronchoscopically). For example, the addition of chondroitin sulfate A or C at concentrations ranging from 0.05-3.00% has a specific and beneficial effect on both the mechanical and biological properties of fibrin gels. Similarly, solutions useful to lavage and adhere tissue can contain comparable amounts of one or more proteoglycans such as syndecan 1-4, decortin, biglycan, CD44, aggrecan, versican, and neuroncan. In one embodiment, the composition of the invention includes ethanol (e.g., 1-20%) fibrinogen (e.g., 0.01-5.00%), HA (e.g., 0.01-3.00%), FN (e.g., 0.001-0.1%), and CS (e.g., 0.01-1.0%). For example, a useful composition of the invention includes 10% ethanol, 0.5% fibrinogen, 0.3% HA, 0.01% FN, and 0.1% CS.

Hyaluronic acid (HA), like CS, is a polysaccharide, consisting of repeating units of glucuronic acid and N-acetylglucosamine joined by a beta 1-3 linkage. However, unlike CS and other GAGs, HA functions in vivo as a free carbohydrate and is not a component of any proteoglycan family. HA is a large polyanionic molecule that assumes a randomly coiled structure in solution and, because of its self-aggregating properties, imparts high viscosity to aqueous solutions. It supports both cell attachment and proliferation. In addition, HA is believed to promote monocyte/macrophage chemotaxis and to stimulate cytokine and plasmin activator inhibitor secretion from these cells. Thus, polysaccharides that include repeating units of, for example, glucuronic acid and N-acetylglucosamine, are useful in achieving tissue volume reduction (e.g., lung volume reduction carried out bronchoscopically). For example, the addition of either high or low MW HA at concentrations ranging from 0.05-3.00% will have a specific and beneficial effect on both the mechanical and biological properties of fibrin gels.

Fibronectin (Fn) is a widely distributed glycoprotein present within the ECM. It is present within tissues as a heterodimer in which the subunits are covalently linked by a pair of disulfide bonds near the carboxyl terminus. Fn is divided into several domains, each of which has a distinct function. The amino terminal region has binding sites for fibrin, heparin, factor XIIIa, and collagen. Fn has a central cell-binding domain, which is recognized by the cell surface integrins of macrophages, as well as fibroblasts, myofibroblasts, and undifferentiated interstitial cells. Fn's primary function in vivo is as a regulator of wound healing, cell growth, and differentiation. Fn can promote binding and chemotaxis of fibroblasts. It can also act as a cell cycle competency factor allowing fibroblasts to replicate more rapidly when exposed to appropriate "progression signals." In vitro, Fn promotes fibroblast migration into plasma clots. In addition, Fn promotes alterations in alveolar cell phenotype that result in a decrease in surfactant expression. Thus, Fn molecules that promote tissue collapse and scar formation are useful in achieving tissue volume reduction (e.g., lung volume reduction carried out bronchoscopically). Fn isoforms generated by alternative splicing are useful, and addition of lysophosphatidic acid, or a salt thereof, can be added to Fn-containing solutions to enhance Fn binding. For example, the addition of a Fn at a concentration ranging from 0.05-3.00% will have a specific and beneficial effect on both the mechanical and biological properties of fibrin gels used, for example, in BLVR.

Poly-L-lysine (PLL) is commonly used in cell culture experiments to promote cell attachment to surfaces, and it is strongly positively charged. Despite its large size, it dissolves readily in the presence of anionic polysaccharides, including HA and CS. Thus, PLL, HA, and CS may be used in combination in solutions to lavage, destabilize, and adhere one portion of a tissue to another. The studies described below explore the possibility that PLL in a fibrin network containing long chain polysaccharides generates ionic interactions that make fibrin gels more elastic and less prone to breakage during repeated stretching. PLL can also promote hydration and swelling once matrices are formed. Thus, a particular advantage of using solutions containing PLL for lung volume reduction is that such solutions make it even less likely that the resulting matrices will be dislodged from the airway. PLL having a molecular weight between 3,000 and 10,000 can be used at concentrations of 0.1 to 5.0%.

The di-peptide proline-hydroxyproline (PHP) is common to the sequence of interstitial collagens (type I and type III). Collagen-derived peptides may act as signals for promoting fibroblast in-growth and repair during the wound healing process. The PHP di-peptide, at concentrations ranging from 2.5-10.0 mM, is as effective as type I and type II collagen fragments in promoting fibroblast chemotaxis in vitro. Thus, PHP di-peptides are useful in achieving tissue volume reduction (e.g., lung volume reduction carried out bronchoscopically). For example, the addition of PHP di-peptides at concentrations ranging from 0.05-3.00% will have a specific and beneficial effect on both the mechanical and biological properties of fibrin gels.

The addition of ECM components to washout solutions and fibrin gels may promote tissue collapse and scarring by modulating the activity of interstitial fibroblasts and lung macrophages. Disruption of intact epithelium tends to promote permanent atelectasis and scarring. Thus, it can be useful to expose the alveolar epithelium to agents that cause inflammation and trigger an "ARDS-like" response. Of course, administration of such agents must be carefully controlled and monitored so that the amount of inflammation produced is not hazardous. Alternatively, tissue repair and volume reduction can be facilitated by the addition of agents that promote epithelial cell apoptosis, "programmed cell death," without extensive necrosis and inflammation. These agents would cause a loss of alveolar cell function without inflammation. One way to produce such a response is by administering sphingomyelin (SGM), a lipid compound that is taken up by certain cell types and enzymatically converted by sphingomyelinase and ceramide kinase to ceramide-1-phosphate, a key modulator of programmed cell death. The application of SGM is also likely to inhibit surfactant, since SGM has anti-surfactant activity in vitro. SGM could be administered in the anti-surfactant washout solution, where it could act specifically on the epithelial surface to destabilize the local surface film and cause epithelial cell death without inflammation. Solutions useful for repairing air leaks in pulmonary tissue or for performing BLVR can contain SGM, or a biologically active variant thereof, at concentrations ranging from 0.05-15.00% (e.g., 0.1, 0.5, 1.0, 2.0, 2.5, 5.0, 7.5, 10.0, 12.0, 13.0, 14.0, or 14.5

The efficacy of BLVR can also be enhanced by modulating the endothelial cell response. For example, transient vasoconstriction can be achieved by including epinephrine or norepinephrine in the washout solution. Sustained endothelial modulation could be achieved by inclusion of one of the endothelins, a family of cytokines that promotes vasoconstriction and acts as a profibrotic agent. Endothelin-1, endothelin-2, or endothelin-3 can be used alone or in combination. Thus, solutions of the invention can also include a vasoactive substance such as endothelin, epinephrine, or norepinephrine (at concentrations ranging from 0.01-5.00%), or combinations thereof. The advantage of including one or more vasoactive substances is that they favorably modulate the vascular response in the target tissue and this, in turn, reduces ventilation perfusion mismatching, improves gas exchange, and, simultaneously, promotes scar formation.

Application of Fibrin-Based, Fibrinogen-Based, and ECM-Containing Compositions Following Lung Collapse While a targeted region of the lung can be collapsed by exposure to one of the substances described above, these substances can also be applied to adhere one region of the lung to another (and to promote fibrosis) when the collapse has been induced by other means. For example, the substances described above can be applied after the lung collapses from blockage of airflow into or out of the targeted region. Such blockage can be readily induced by, for example, inserting a bronchoscope into the trachea of an anesthetized patient, inserting a balloon catheter through the bronchoscope, and inflating the balloon so that little or no air passes into the targeted region of the lung. Collapse of the occluded region after the lung is filled with absorbable gas would occur over approximately 5-15 minutes, depending on the size of the region occluded. Alternatively, a fibrinogen- or fibrin-based solution (e.g. a fibrinogen- or fibrin-based solution that contains a polypeptide growth factor), as well as solutions that contain components of the ECM (such as those described herein), ECM-like agents (such as PLL and PHP), vasoactive substances (i.e., substances that cause vasoconstriction), and pro-apoptotic factors (e.g., proteins in the Bcl-2, caspase, and annexin families) can be applied after the lung is exposed to another type of anti-surfactant (e.g., a non-toxic detergent).

Of course, the compositions described herein are useful not only in the course of performing BLUR, but also for sealing tears in the lung that arise from trauma or in the course of any surgical procedure.

Catheters for Application of Material to the Lung

Figure 2A:
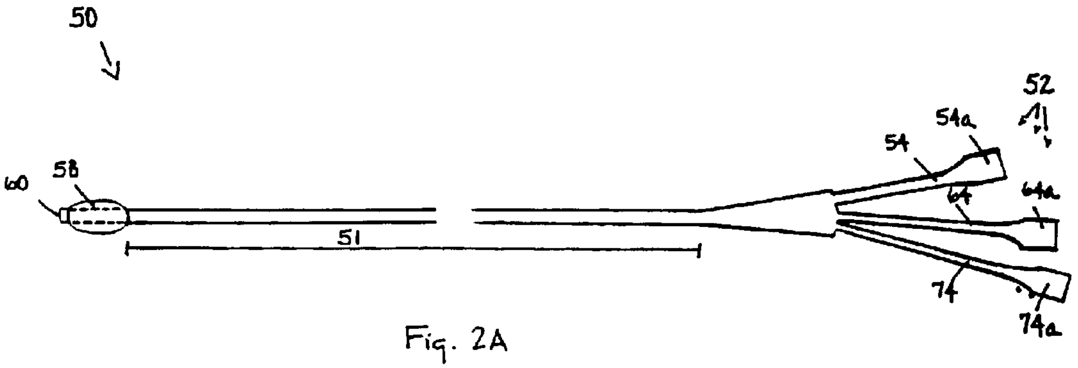
FIG. 2*a* illustrates a catheter that can be inserted through a bronchoscope.

Referring to FIG. 2*a*, any of the solutions described above can be administered to the lung by a balloon catheter 50 having multiple ports 52 through which materials (such as solutions or suspensions) or gases (such as air) can be injected via a corresponding number of lumens.

The ports of catheter 50 are arranged as follows. A first port 54 having a proximal end 54*a* adapted for connection with a gas supply (e.g., a leur-lock syringe containing air) communicates with internal lumen 56 of catheter 50, which terminates within inflatable balloon 58 near distal tip 60 of catheter 50. A second port 64 having a proximal end 64*a* adapted for connection with a source of one or more materials (e.g., medication cartridge 80. described below) communicates with internal lumen 66, which terminates at open distal tip 60 of catheter 50. A third port 74 having a proximal end 74*a* adapted for connection with a source of one or more materials (e.g., medication cartridge 80) communicates with internal lumen 76, which also terminates at open distal tip 60 of catheter 50.

Thus, gas injected through port 54 travels through internal lumen 56 to inflate balloon 58, and material injected through port 64 and/or port 74 travels through internal lumens 66 and 76, respectively, to distal tip 60 of catheter 50. Upon reaching distal tip 60 of catheter 50, materials previously separated within lumens 66 and 76 would mix together.

Figure 2B:
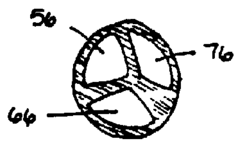
FIG. 2*b* is a cross-sectional view through the shaft of the catheter illustrated in FIG. 2*a*.

Referring to FIG. 2*b*, internal lumen 54, internal lumen 64, and internal lumen 74 are shown in a cross-sectional view of shaft 51 of catheter 50. In another embodiment, lumens 66 and 76 can differ in size, with the diameter of the lumen through which the fibrinogen-based solution is applied being approximately twice as great as the diameter of the lumen through which the solution containing the fibrinogen activator is applied.

Figure 2C:
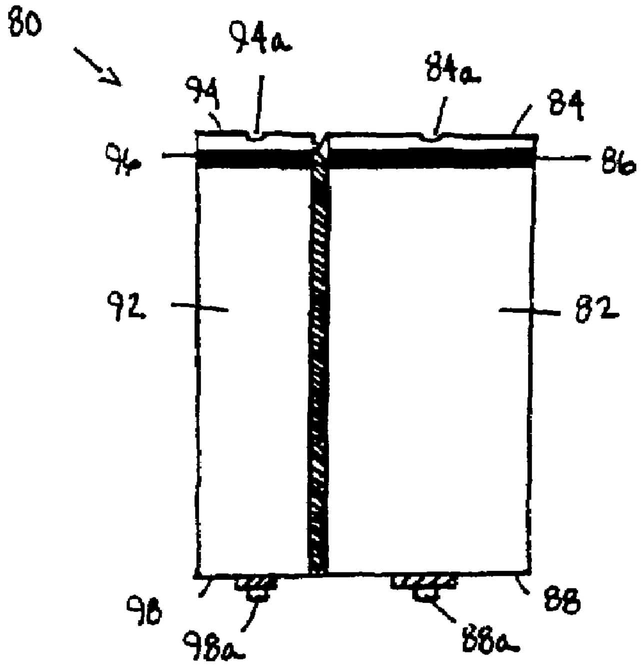
FIG. 2*c* illustrates a cartridge that can be attached to the catheter illustrated in FIG. 2*a*.

Referring to FIG. 2*c*, cartridge 80 can be attached to catheter 50 to inject material via ports 64, 74 and lumens 66, 76. Cartridge 80 includes a first chamber 82 and a second chamber 92, either or both of which can contain material useful in BLVR (e.g., chamber 82 can contain a mixture of fibrinogen, TGF-β, and gentamycin, and chamber 92 can contain thrombin in a calcium-buffered solution). Material within cartridge 80 can be administered to the lung by way of catheter 20, as follows. Upper wall 84 of chamber 82 includes orifice 84*a*, through which pressure can be applied to depress plunger 86. Depression of plunger 86 forces material within chamber 82 toward lower wall 88 of chamber 82, through opening 88*a*, and, when cartridge 80 is attached to catheter 50, into port 64 of catheter 50. Similarly, upper wall 94 of chamber 92 includes orifice 94*a*, through which pressure can be applied to depress plunger 96. Depression of plunger 96 forces material within chamber 92 toward lower wall 98 of chamber 92, through opening 98*a*, and, when cartridge 80 is attached to catheter 50, into port 74 of catheter 50.

Figure 2D:
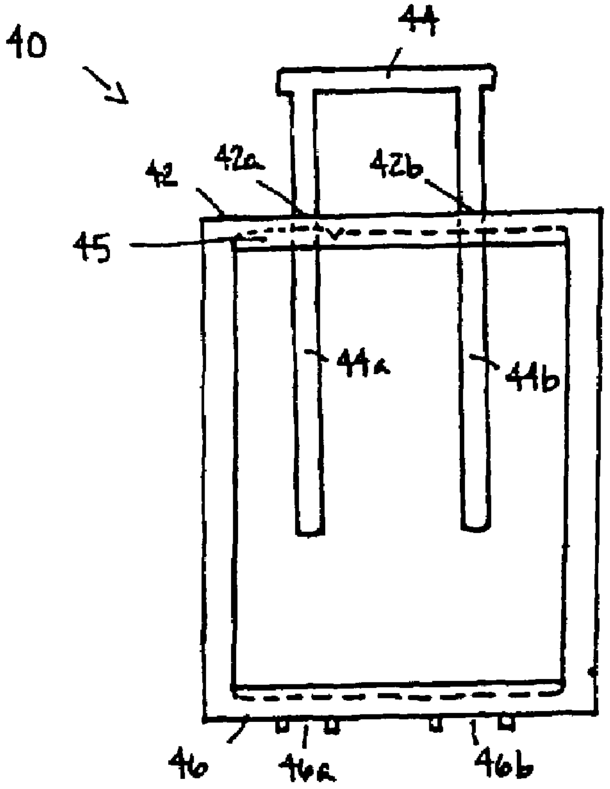
FIG. 2*d* illustrates an injector that can be used to expel material from the cartridge illustrated in FIG. 2*c*.

Referring to FIG. 2*d*, to aid the transfer of material from cartridge 80 to catheter 50, cartridge 80 can be placed within recess 45 of a frame-shaped injector 40. Injector 40 includes upper wall 42, having orifices 42*a* and 42*b*, through which arm 44 is inserted. Prong 44*a* of arm 44 enters injector 40 through orifice 42*a* and prong 44*b* of arm 44 enters injector 40 through orifice 42*b*. When cartridge 80 is placed within injector 40 and arm 44 is depressed, prongs 44*a* and 44*b* are forced against plungers 86 and 96, respectively, thereby extruding materials in chambers 82 and 92 through openings 88*a* and 98*a*, respectively, of cartridge 80 and openings 46*a* and 46*b*, respectively, of lower wall 46 of injector 40.

Figure 2E:
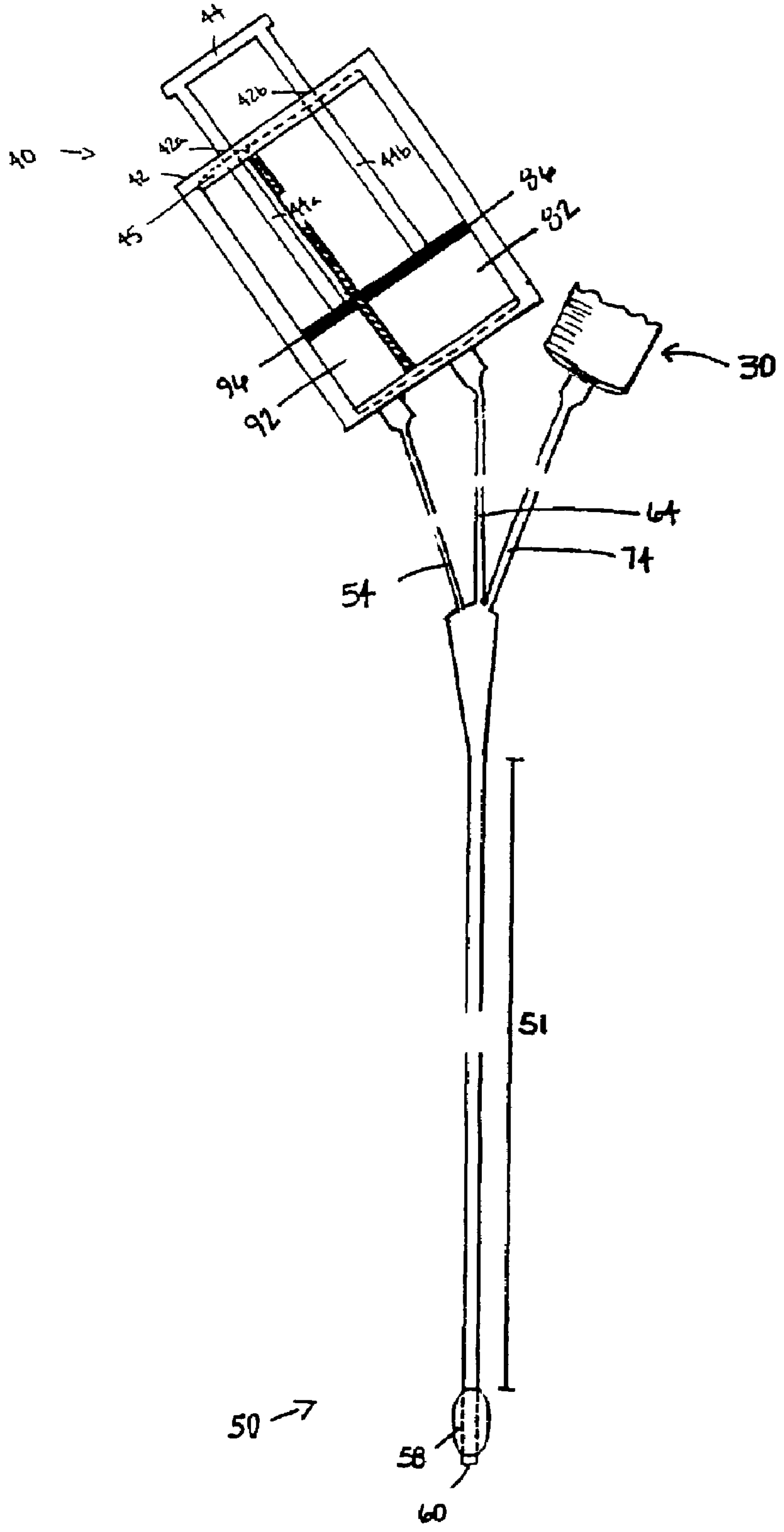
FIG. 2*e* illustrates the catheter of FIG. 2*a* assembled with the cartridge of FIG. 2*c*, the injector of FIG. 2*d*, and a leur-lock, air-filled syringe.

FIG. 2*e* illustrates catheter 50 assembled with cartridge 80, injector 40, and a leur-lock, air-filled syringe 30.

Figures 13A, 13B, 13C:
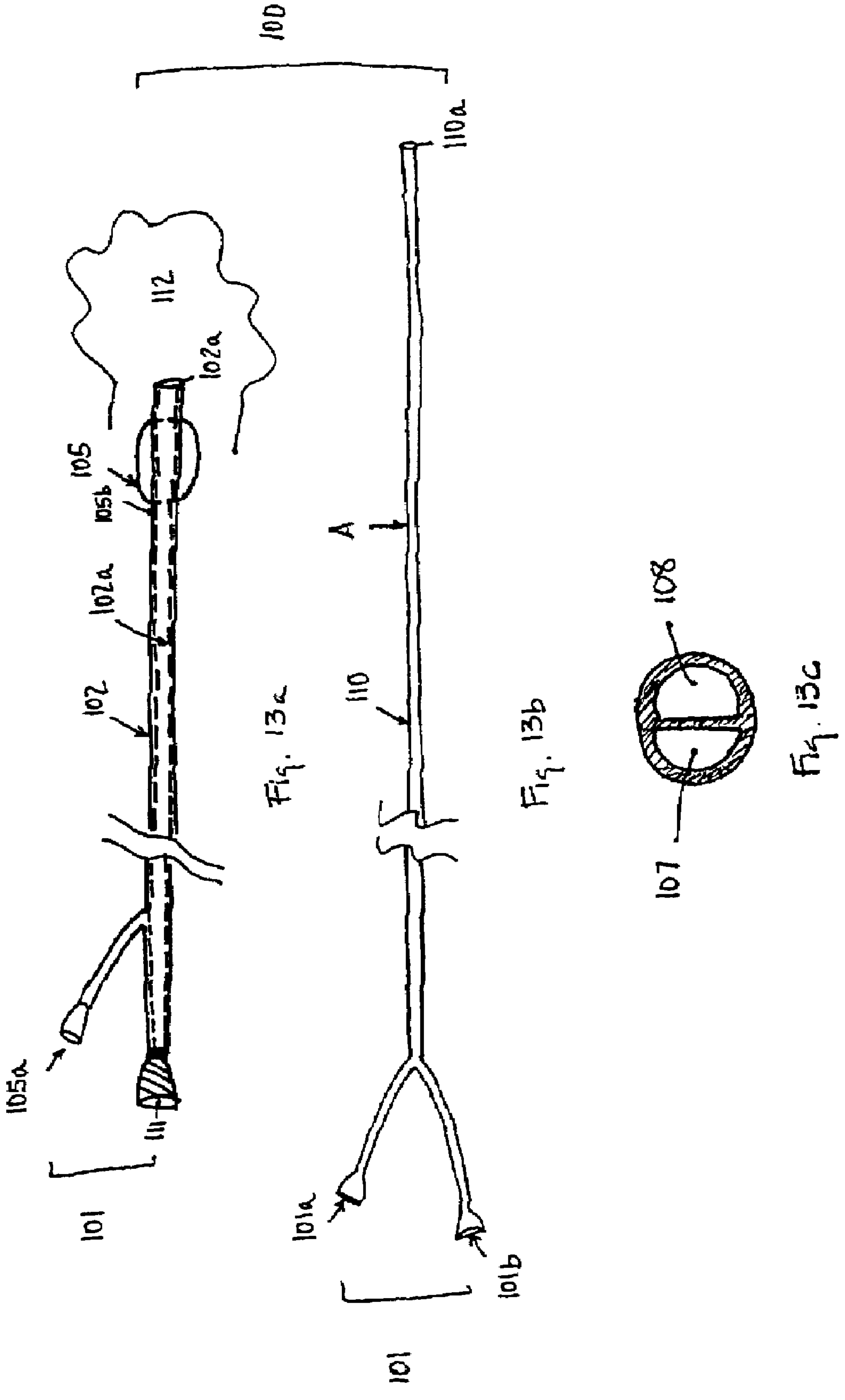
FIGS. 13*a*, 13*b*, and 13*c* are schematics of a dual-lumen catheter system.

Referring to FIGS. 13*a* through 13*c*, any of the solutions described herein can be administered to the lung by a balloon catheter 100 having multiple ports 101 through which materials (such as solutions or suspensions) or gases (such as air) can be injected via a corresponding number of lumens. Catheter 100 features a dual sheath for delivery of the compositions of the invention. Outer sheath 102 encloses inner channel 102*a* through which inner sheath 110 passes. Outer sheath 102 supports balloon 105. Air (or another gas or substance) injected through proximal inflation port 105*a* flows through lumen 105*b* to balloon 105, thereby sealing region 112. When inner sheath 110 resides within inner channel 102*a* and balloon 105 is inflated, compositions (e.g. anti-surfactant solutions) can then be applied through distal port 111 to sealed region 112. Sealed region 112 can be exposed to a solution (e.g., an anti-surfactant or wash-out solution) for a brief time (e.g. 60 seconds). The solution can then be removed through distal port 111 under continuous suction. Typically, suction will be applied for 3-5 minutes. Inner sheath 110 is then passed through inner channel 102*a* of outer sheath 102. By virtue of the fact that inner sheath 110 is longer than outer sheath 102, distal tip 110*a* of inner sheath 110 comes to rest deeper within sealed region 112 than distal tip 102*a* of outer sheath 102. A fibrin- or fibrinogen-based solution can then be administered through one of multiple ports 101. Alternatively, a fibrin-based solution can be administered through proximal port 101*a* and a polymerizing agent (e.g. thrombin) can be administered through proximal port 101*b*. An advantage of the dual lumen catheter system represented in FIGS. 13*a* and 13*b* is that inner sheath 110 can be manually withdrawn through inner channel 102*a* as solutions are being injected through proximal ports 101*a* and 101*b*. Thus, solution(s) can be distributed (i.e. spread) from the most distal reaches of distal tip 110*a* to the point where inner sheath 110 is withdrawn through distal tip 102*a*. As shown in FIG. 13*c*, a cross-sectional view through inner sheath 110 at point A, dual lumens 107 and 108 keep the solutions injected through proximal ports 101*a* and 101*b* separate until they emerge through distal tip 110*a* into sealed region 112.

Accordingly, the invention features a respiratory catheter system that includes an outer sheath defining a first lumen, the outer sheath including a fixation member (e.g., a balloon) for locating the outer sheath in the bronchial tree, and an inner sheath configured to be movably received within the first lumen, the inner sheath being defined by a pair of lumens each for receiving one of a first and second components of a glue.

Figures 14A, 14B:
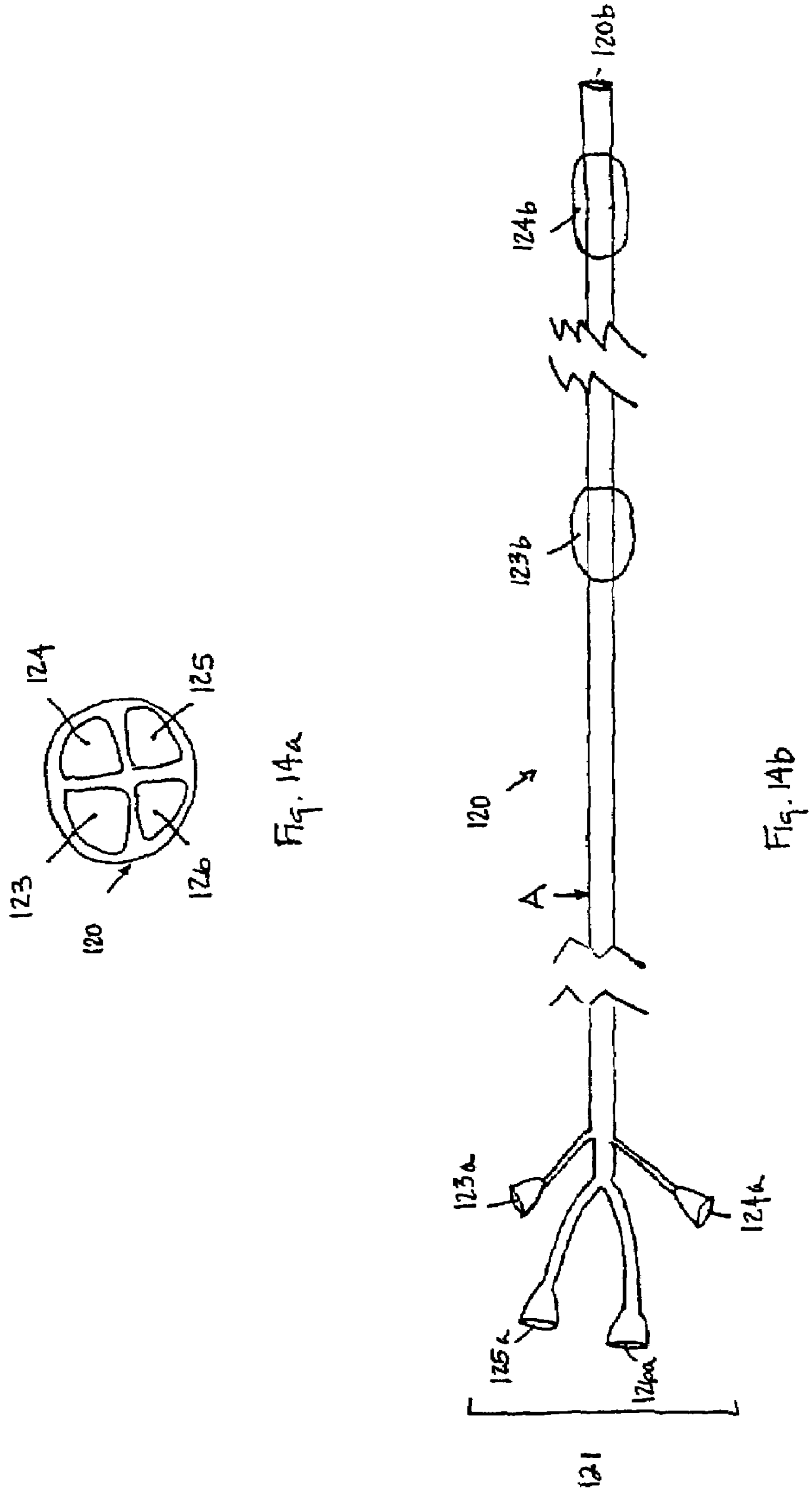
FIGS. 14*a* and 14*b* are schematics of a catheter system that can be used to seal bronchoplueral fistulas.

Referring to FIGS. 14*a* and 14*b*, any of the solutions described herein can be administered to the lung by a dual-balloon catheter 120 having multiple ports 121 through which materials (such as solutions or suspensions) or gases (such as air) can be injected via a corresponding number of lumens. Catheter 120 features four channels. These channels are shown in FIG. 14*a* in cross section taken at point A of FIG. 14*b*. Channel 123 connects balloon port 123*a* with balloon 123*b*. Channel 124 connects balloon port 124*a* with distal balloon 124*b*. Channel 125 connects injection port 125*a* with distal tip 120*b*, and channel 126 connects injection port 126*a* with distal tip 120*b*. The advantage of this catheter is that it reduces the length of time it takes to perform BLVR by allowing the physician to determine more quickly whether distal tip 120*b* has reached an appropriate region of the lung (e.g. a region that is leaking air). The bronchi and bronchioles branches extensively (see FIG. 1), and it is desirable to place the cathether as accurately as possible within the bronchial tree. Typically, the physician will know when an air leak has been sealed by watching for movement of air from a tube placed in the patient's chest prior to BLVR. If catheter 120 is inserted (e.g. through a bronchoscope) into one of the branches of the bronchial tree and if air movement through the chest tube ceases when proximal balloon 123*b* is inflated, the physician will know that the damaged region of the lung lies distal to balloon 123*b*. If balloon 123*b* is subsequently deflated, balloon 124*b* is inflated, and air movement through the chest tube ceases, the physician will know that distal tip 120*b* is also in the appropriate region of the lung. If, however, movement through the chest tube continue (when balloon 123*b* is deflated and balloon 124*b* is inflated) then distal tip 120*b* has not been advanced into the region of the lung that is leaking and in need of repair.

Accordingly, the invention features respiratory catheter system that includes a sheath defining four lumens, wherein the first and second lumens receive the first and second components of a glue and extend from the proximal end of the catheter to the distal tip of the catheter, and the third and fourth lumens extend from the proximal end of the catheter to fixation members (e.g., balloons) positioned along the shaft of the catheter, one fixation member being positioned closer to the distal tip of the catheter than the other.

The preferred methods, materials, and examples that will now be described are illustrative only and are not intended to be limiting; materials and methods similar or equivalent to those described herein can be used in the practice or testing of the invention.

Example 1

BLVR in an Isolated Calf Lung

Isolated calf lungs are excellent models for BLUR because they are easy to work with and anatomically similar to human lungs. Calf lungs having 4-5 liters total lung capacity were purchased from Arena and Sons' Slaughter House (Hopkinton, Mass.) and delivered on ice to the laboratory within 3 hours of procurement. The lungs were tracheally cannulated with a #22 tubing connector and suspended from a ring clamp with the diaphragmatic surface resting in a large Teflon dish containing 2-3 mm of phosphate buffered saline (PBS). The visceral pleural surface was kept moist by spraying it with a mist of 0.15 M NaCl at regular intervals. Pleural leaks were identified by the appearance of bubbles on the pleural surface and by assessing the lungs' ability to hold a constant pressure of 20 cm $H_2O$ inflation pressure. Leaks were sealed by autologous buttress plication. Any adversely affected sections of the lungs were rolled up and stapled in a manner similar to that used in LVRS in humans (Swanson et al., *J. Am. Coll. Surg.* 185:25-32, 1997).

Absolute lung volumes were measured by gas dilution using nitrogen as the tracer gas (Conrad et al., *Pulmonary Function Testing—Principles and Practice*, Churchill Livingstone Publishers, New York, N.Y., 1984). Measurements were performed at 0 cm $H_2O$ transpulmonary pressure as follows. A three liter syringe was filled with 1.5 liters of 100% oxygen from a reservoir bag. The isolated lung, containing an unknown volume of room air (79% nitrogen) was then connected in-line with the syringe containing 0% nitrogen via a three way valve. The gas was mixed well by depressing the plunger of the syringe 60-100 times, and the equilibrium concentration of nitrogen was then determined using a nitrogen meter (Medtronics, Model 830 Nitrogen meter). The unknown starting lung volume of room air was then calculated according to the following conservation of mass equation:

$$VL=\{F_{N2f}/(0.79-F_{N2f})\}\cdot 1.5\text{ L}$$

where $F_{N2f}$ is the fraction of nitrogen measured at steady state following mixing with 1.5 liters of oxygen from the syringe. This measurement defines the single absolute lung volume that is required to characterize static lung mechanics.

Quasi-static deflation pressure volume curves (QSPVC) were then recorded during step-wise deflation from 20 cm $H_2O$ to 0 cm $H_2O$ transpulmonary pressure as follows. Lungs were filled with air to 20 cm $H_2O$ transpulmonary pressure, and the trachea was then occluded manually. Transpulmonary pressure was recorded using a 50 cm $H_2O$ pressure transducer positioned at the airway opening. Expired lung volume was measured using a pneumotachograph (Hans Rudolf Inc, Kansas City, Mo.) connected in series with the tracheal cannula. Pressure as a function of expired lung volume (referenced to the starting volume at 20 cm $H_2O$) was determined by intermittently occluding the trachea. Occlusions were maintained long enough to allow for equilibration of tracheal and alveolar pressures (no change in tracheal pressure over three seconds). By combining the single absolute lung volume measurement made by nitrogen dilution at zero transpulmonary pressure with QSPVC data, complete static recoil pressure volume relationships were determined. These relationships can be described as an exponential function according to the equation of Salazar et al. (*J. Appl. Physiol.* 19:97-104, 1964):

$$V(P)=V_{max}-Ae^{-kP}$$

where V is lung volume as a function of transpulmonary pressure; P is transpulmonary pressure; $V_{max}$ is the extrapolated lung volume at infinite pressure (approximately equal to TLC); A is the difference between $V_{max}$ and the volume of gas trapped within the lung at zero transpulmonary pressure (approximately equal to vital capacity); and k is the shape factor which describes the curvature of the exponential relationship between pressure and volume independent of the absolute volume of the lung. The parameters $V_{max}$, A, and k were determined from a best fit linear regression analysis, and recoil pressure at total lung capacity (PTLC) determined by direct measurement.

It is useful to express the pressure volume relationship in terms of the parameters described above because each parameter is known to change in a characteristic fashion in emphysema. Thus, one can anticipate specific changes following interventions designed to either produce emphysema (e.g. papain exposure in the animal model) or correct the abnormalities of emphysema (e.g., volume reduction; see Gibson et al., *Am. Rev. Resp. Dis.* 120:799-811, 1979). For example, $V_{max}$ increases in emphysema due to lung hyper-expansion (this reflects an increase in total lung capacity); k, the shape factor, also increases due to a decrease in the slope of the pressure volume relationship at low lung volumes; and A, the difference between maximal lung volume and trapped lung gas at zero transpulmonary pressure, decreases because trapped gas increases out of proportion to total lung capacity. These abnormalities will improve following effective lung volume reduction.

Following completion of lung volume and QSPVC measurements, lung function was assessed during simulated tidal ventilation. A solenoid driven computer controlled pneumatic ventilator was developed for this purpose. This device allows for measurements of lung resistance and dynamic elastance during oscillatory ventilation, while monitoring and maintaining a constant user specified mean airway pressure. Flow (V) into and out of the lung was measured using a pneumotachometer, volume (V) was determined by integration of the flow signal, and transpulmonary pressure (Ptp) was recorded as airway opening pressure referenced to atmospheric pressure.

The flow pattern chosen for measuring lung function was an optimal ventilation waveform (OVW) pattern developed by Lutchen et al. (*J. Appl. Physiol.* 75:478-488, 1993). This pattern represents the sum of a series of sinusoids selected to provide tidal ventilation while simultaneously minimizing signal distortion due to nonlinear effects of the respiratory system (Suki et al., *J. Appl. Physiol.* 79(2):660-671, 1995). Lung function was assessed by determining impedance, the ratio of pressure to flow in the frequency domain, by Fourier analysis. The real and imaginary parts of the impedance signal represent lung resistance and lung reactance, respectively. Lung resistance is, in turn, equal to the sum of tissue resistance ($R_{ti}$) and airway resistance ($R_{aw}$), while lung reactance is determined by a combination of elastance and gas inertance effects. Thus, in contrast to standard sinusoidal or constant flow ventilation, OVW measurements allow for the determination of airway resistance, tissue resistance, and dynamic elastance (Edyn) over a range of frequencies from a single measurement. This detailed information is useful for several reasons. Volume reduction is a procedure which has the potential for affecting all three of these lung function parameters. In emphysema, volume reduction should reduce $R_{aw}$ by improving airway tethering, thereby stretching airways open. Because volume reduction increases tissue stretching, however, it will tend to increase tissue resistance. Total lung resistance, the sum of $R_{aw}$ and $R_{ti}$, can therefore be variably affected depending upon how LVR individually affects $R_{aw}$ and $R_{ti}$. In most instances, there should be some optimal range of tissue resection that can produce a substantial decrease in $R_{aw}$, but only a small increase in $R_{ti}$. The OVW approach helps define this optimum. An additional benefit of the OVW approach is that it provides a non-invasive assessment of lung function heterogeneity. The presence of heterogeneity, which physiologically produces a positive frequency dependence in lung elastance, can be detected by the OVW technique (Lutchen et al., *J. Appl. Physiol.* 75:478-488, 1993). In the normal lung, elastance is relatively frequency independent since most regions have similar mechanical properties leading to uniform gas flow distribution. In a diseased lung, regional differences in impedance to gas flow exist, and elastance increases with increasing frequency. In emphysema, frequency dependence of elastance is a characteristic finding and reflects regional differences in disease severity. A successful volume reduction targeted at a diseased region should reduce heterogeneity and frequency dependence of elastance. Thus, reduction in frequency dependence of elastance can be used as an index of a successful BLVR procedure, and can be readily determined from the OVW measurement. It is expected that any measurement made immediately following BLVR would underestimate the improvement that will become evident once a mature scar has formed. At that time, a 25-50% improvement in expiratory flow rates could be observed. Thus, any fibrin- or fibrinogen-based composition described above is within the scope of the invention if, when applied according to a BLVR procedure, it produces a 25-50% improvement in expiratory flow rates.

Measurements of lung volumes, quasi-static pressure volume relationships, and lung resistance and dynamic elastance as functions of frequency were determined in three isolated, naive calf lungs before and after plication volume reduction. Dynamic recordings were made at 9-10 cm $H_2O$ mean transpulmonary distending pressure (PEEP=5 cm $H_2O$) via the OVW technique at tidal volumes of 10% of measured $V_{max}$. Small leaks present following plication were sealed with cyanoacrylate glue. The estimated time between initial and post-reduction recordings was between 60 and 90 minutes.

Pre- and post-volume reduction lung physiology recordings in the isolated calf lung are summarized below in Table 1.

TABLE 1

Static and Dynamic Lung Mechanics Measured in Isolated Calf Lungs Before and Following Plication Lung Volume Reduction

| | Raw (0.2 Hz) (cm $H_2O$/L/sec) | | Rti (0.2 Hz) (cm $H_2O$/L/sec) | | (cm $H_2O$/L) | | Edyn Vmax (liters) | |
|---|---|---|---|---|---|---|---|---|
| Lung | pre | post | pre | post | pre | post | pre | post |
| 1 | 0.42 | 0.48 | 1.31 | 1.30 | 18.1 | 22.2 | 4.4 | 3.8 |
| 2 | 1.10 | 0.85 | 1.60 | 2.36 | 26.3 | 29.4 | 3.5 | 3.1 |
| 3 | 0.82 | 0.88 | 3.08 | 2.92 | 40.1 | 36.2 | 2.9 | 2.7 |
| Mean | 0.78 | 0.74 | 2.00 | 2.19 | 28.2 | 29.2 | 3.6 | 3.2 |
| Std dev | 0.34 | 0.22 | 0.49 | 0.82 | 11.1 | 7.0 | 0.75 | 0.56 |

These results indicate that, in normal calf lungs, a 10-15% volume reduction (mean 11.1%) produces no significant change in dynamic elastance, airway resistance, or tissue resistance. They further demonstrate that detailed function can be measured in isolated lungs using the measurement system described herein and that successful plication volume reduction can be performed on isolated lungs, which serve as controls for BLVR experiments.

Example 2

Fibrinogen-Based Anti-Surfactants

Mechanical equilibrium across the alveoli and small airways is determined by a balance between distending forces, which are exerted by transpulmonary gas pressure pushing outward, and recoil forces, which are exerted by parenchymal tissue structures and the surface film lining the air liquid interface, both of which pull inward and act to promote lung collapse. For the alveoli and small airways to remain patent during normal breathing. destabilizing force perturbations must be balanced by intrinsic stabilizing forces. The tendency for the lung to resist destabilization and atelectasis can be expressed in terms of two biomechanical properties: the bulk modulus (K) and the shear modulus (p). The value of K is proportional to the lung's ability to resist distortion resulting from forces directed perpendicular (or normal) to a region of tissue (Martinez et al., *Am. J. Resp. Crit. Care Med.* 155: 1984-1990, 1997), and the value of p is proportional to the lung's ability to resist distortion resulting from shearing forces imposed on a region of tissue (Stamenovic, *Physiol Rev.* 70:1117-1134, 1990). The larger the values of K and p, the greater the tendency of intrinsic forces within the lung to resist external perturbations and atelectasis. Conversely. any factors which lower K and p tend to promote alveolar instability and collapse resulting in atelectasis. The values of the shear and bulk moduli depend on both tissue and surface film properties and can be quantitatively expressed as (Stamenovic, *Physiol Rev.* 70:1117-1134, 1990):

$$K=\tfrac{1}{3}\{(B-2)\cdot P_{tis}\}+\tfrac{1}{3}\{(3b-1)\cdot P_{\gamma}\}$$

$$\mu=(0.4+0.1B)\cdot P_{tis}+0.4\cdot P_{\gamma}$$

where B is a normalized elastance for the tissue components (elastin, collagen, and interstitial cells) of the lung; $P_{tis}$ is the recoil pressure of tissue components in the absence of surface film recoil; b is a normalized elastance for the surface film at the air-liquid interface; and $P_{\gamma}$ is the recoil pressure of the surface film in the absence of tissue recoil. In the healthy lung, surface forces account for two-thirds to three-quarters of lung recoil, and thus the contribution of the $P_{\gamma}$ terms to the bulk and shear moduli are primarily responsible for determining stability. In emphysema, where tissue elements are destroyed and exert less recoil, the role of surface forces in determining parenchymal stability is of even greater importance.

The primary goal of these experiments was to develop a biocompatible reagent that could be instilled bronchoscopically to produce site-specific alterations in surface film behavior so as to promote alveolar instability and collapse (i.e., to develop an anti-surfactant). This can be achieved if the liquid film lining the alveoli and small airways undergoes a reduction in bulk and or shear moduli as a result of chemical modification. In essence, this requires a solution that can alter the surface tension lowering properties of native lung surfactant without producing other undesired effects. From a biomedical perspective, the characteristic parameter of the surface film which can be most readily affected by such external chemical manipulation is the dimensionless film elastance prameter, b, which is equal to b'(δγ/δA)(V/A), where γ is the surface tension of the film; A is the area of the surface over which the film is spread, and b' is a proportionality constant that varies depending upon the geometry of the region in question. For normal lung surfactant (δγ/δA)(V/A) (define as b*=b/b') assumes values of approximately 100-110. As b decreases (i.e. δγ/δA becomes smaller or y becomes larger) within a given region, the local surface forces act more to destabilize rather than stabilize the alveoli. Thus, films with low elastance (relatively flat surface tension versus surface area profiles) or elevated surface tensions tend to promote destabilization.

Figure 3A:
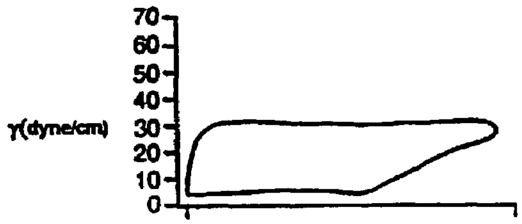
FIGS. 3*a* and 3*b* are graphs depicting the surface tension vs. surface area of surfactant films from a control guinea pig (FIG. 3*a*) and a guinea pig exposed to LPS (FIG. 3*b*).
Figure 3B:
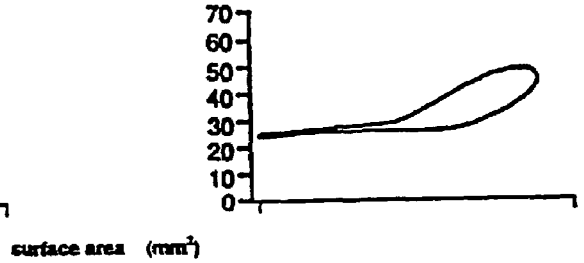

Examples of stable and unstable surface films displaying these patterns of behavior are shown in FIGS. 3*a* and 3*b*. FIG. 3*a* shows a surface tension-surface area profile measured by pulsating bubble surfactometry (PBS) for normal surfactant at 1 mg/ml concentration isolated from the lung of a normal guinea pig. It demonstrates both a positive film elastance (δγ/δA>0) and low minimum surface tension ($\gamma_{min}$<3 dyne/cm). Such a film possesses positive values for the biophysical parameters b, K, and p and thus would promote stability in vivo. In contrast to normal surfactant, a sample isolated from an animal with acute lung injury and atelectasis following endotoxin infusion shows nearly zero elastance and an elevated minimum surface tension (FIG. 3*b*). This film has a bulk modulus of less than zero, and thus would promote alveolar instability and collapse. While these biophysical features are detrimental in the setting of acute lung injury, the ability to impose such features on a film in a controlled fashion is obviously desirable in conducting the present experiments.

Because the dysfunction observed above occurs in vivo, characterizing the biochemical changes in surfactant that accompany this dysfunction will suggest biocompatible reagents that are useful in BLVR. Surfactant samples isolated from animals treated with lipopolysaccharide (LPS) are in large part dysfunctional as a result of alterations in interfacial properties due to mixing with serum proteins, which have entered the alveolar compartment across the damaged basement membrane (Kennedy et al., *Exp. Lung Res.* 23:171-189, 1997).

To determine whether fibrinogen solutions could be added to native surfactant to produce significant surface film dysfunction, calf surfactant was isolated by lavage and centrifugation from calf lungs provided fresh from a local slaughter house. Bovine fibrinogen was purchased commercially (Sigma Chemical Co., St. Louis, Mo.). Stock solutions of each reagent were prepared in normal saline, and mixed at mg ratios (fibrinogen to surfactant phospholipid content) of 0.1:1, 0.5:1, 1.0:1, 5.0:1, and 10.0:1. The results were compared to mixtures of calf lung surfactant and bovine serum albumin.

Figure 4A:
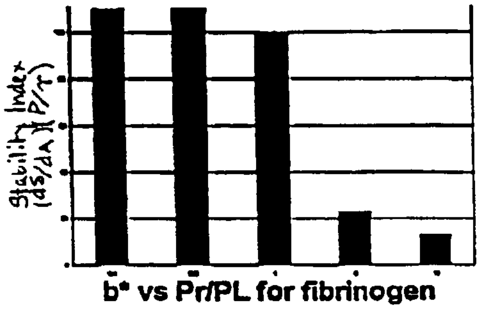
FIGS. 4*a* and 4*b* are bar graphs depicting the surface film stability parameter (Gy/dA)1(A/y) as a function of protein/lipid concentration for fibrinogen and albumin surfactant mixtures.
Figure 4B:
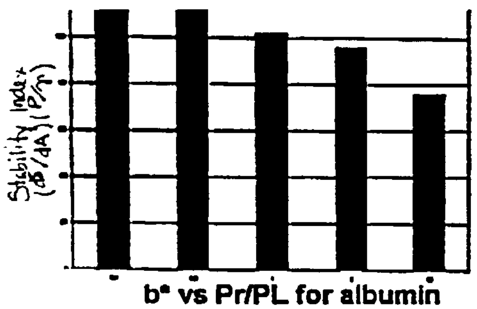

Surface tension recordings were made by pulsating bubble surfactometry at 37° C., oscillation frequency of 20 cycles/min, and area amplitude ratio of 72%, continuously, for 5 minutes (Enhorning, *J. Appl. Physiol.* 43:198-203, 1977). Based on measurements of surface tension versus surface area, values for the film stability parameter, (γδ/δA)/(A/γ), were determined and expressed as a function of protein to phospholipid concentration ratio. The results are summarized in FIGS. 4*a* and 4*b*. These results suggest that fibrinogen is a more potent inhibitor of surfactant function than albumin and is able to generate marked surface film instability (expressed in terms of the film stability criteria b*, at protein to lipid concentration ratios of less than 5:1). These concentration ratios are readily achievable in vivo using concentrated fibrinogen solutions.

To test fibrinogen solutions in isolated calf lungs, stock solutions of bovine fibrinogen (Sigma Chemical, St. Louis, Mo.) in 5 mM Tris-HCl (pH 7.4) and partially purified thrombin in 5 mM Tris-HCl containing 5 mM $CaCl_2$, were prepared. Mixing studies demonstrated that ratios of fibrinogen to thrombin of between 10:1 to 3:1 (mg:mg) resulted in polymerization within 3-5 minutes. A ratio of 10:1 was selected for whole lung testing. Isolated calf lungs were cannulated, suspended from a ring clamp, and subjected to baseline lung volume and QSPVC measurements as described above. At zero transpulmonary pressure under direct bronchoscopic visualization, the bronchoscope was wedged in a distal subsegment approximately 5 mm in diameter. The subtended surface was then lavaged with 50 mls of fibrinogen solution (10 mg/ml) injected through a P-240 polypropylene catheter passed through the suction port. The fibrinogen solution was stained with several drops of concentrated Evans blue to allow for ready identification of the target region. The catheter was then removed, and suction was applied directly through the suction port of the scope to complete the rinsing procedure. Lavage return averaged 28 mls in the 4 lavage procedures performed (56% return). The catheter was then replaced into the affected region and 4 mls of thrombin in calcium containing buffer were instilled. A second lavage and polymerization procedure was then performed in a different subsegment. Repeat lung volumes and quasi-static pressure volume profiles were then recorded. The results are summarized in Table 2.

TABLE 2

Effect of Fibrinogen Instillation and Polymerization on Lung Volumes

| | Pre-instillation Volume (L) | Post-instillation volume (L) |
|---|---|---|
| Lung #1 | 3.4 | 2.9 |
| Lung #2 | 3.1 | 2.8 |

These data indicate that even without the addition of factor XIIIa to promote clot stabilization, reductions in lung volume were achieved that significantly exceeded the retained volume of polymerizing solution, indicating that sustained collapse had been achieved.

Example 3

Fibrinogen- and Fibrin-Based Solutions Containing Growth Factors

Any potential anti-surfactant can be evaluated in the assay described above, which demonstrated that fibrinogen solutions possess many of the features desired for an anti-surfactant. In addition to the fibrinogen solution described above, one can use solutions that impart additional characteristics to compositions that can be used to perform BLUR in vivo. For example, the fibrinogen solution can be modified to support fibroblast growth and to serve as a reservoir for antibiotics. Any modified fibrinogen solution can be used in conjunction with factors that promote fibrosis so long as the fibrinogen maintains the ability to inhibit surfactant and undergo polymerization.

Basic fibroblast growth factor (bFGF) and/or transforming growth factor-beta (TGFβ) can be added to solutions of fibrinogen, as can an antibiotic mixture of ampicillin and gentamicin, which can be added in amounts sufficient to exceed the minimal inhibitory concentration for most bacteria.

In vitro studies can be conducted to determine appropriate concentrations of factor XIIIa relative to fibrinogen and thrombin, and assess how growth factors and antibiotics affect this final cross-linking step. The surface tension of surfactant fibrinogen mixtures can be measured in vitro using a commercially available pulsating bubble surfactometer (PBS) unit. Measurements of surface tension as a function of surface area can be performed at 37° C., oscillation frequency of 20 cycles/min, and a relative surface area change that approximates that of tidal breathing (δA/A=20-30%).

Equilibrium and dynamic surface tension recordings can also be made. Recordings can be performed at 30 seconds, 5 minutes, and 15 minutes to ensure that any surface film dysfunction observed initially is sustained throughout the measurement period. The stability of each film preparation can be expressed in terms of b*, the dimensionless surface film elastance ($\delta\gamma/dA \cdot A/\gamma$) described above normalized to b* values measured for native calf lung surfactant. Mixtures displaying normalized b* values of <0.2 would be acceptable for additional testing as anti-surfactants.

Calf lung surfactant can be isolated from whole calf lungs as previously described (Kennedy et al., *Exp. Lung Res.* 23:171-189, 1997), and bovine fibrinogen, bFGF, factor XIIIa transglutaminase, and TGF can be purchased from commercial suppliers (e.g., Sigma Chemical Co., St. Louis, Mo.).

Surface tension behavior for samples with fibrinogen:surfactant ratios ranging between 0.01 to 10 (mg protein:mg lipid) can be prepared in phosphate buffered saline (0.15 M, pH 7.3). The following six mixtures were chosen because they are representative of mixtures that may be useful in vivo, and they contain components of partially polymerized fibrin that may exist within the lung during the process of polymerization. Thus, they represent the behavior of partially polymerized mixtures in vivo and can be assessed to determine whether the ability of fibrinogen to inhibit surfactant function changes as it undergoes polymerization.

Test mixtures will include surfactant (at 1 mg/ml) with appropriate amounts of: (1) fibrin monomer alone; (2) fibrin monomer with FGF and TGFβ; (3) fibrin monomer with FGF, TGFβ, ampicillin, and gentamicin; (4) fibrinogen with FGF and TGFβ; (5) fibrinogen with FGF, TGFβ, ampicillin, and gentamicin; and (6) fibrinogen with FGF, TGFβ, ampicillin, gentamicin, and thrombin. Recordings will be discontinued for the samples that undergo polymerization during surface film measurements (thereby making measurements of γ vs A impossible), and the time to polymerization will be noted.

Clot stability can be tested in vitro on solutions of surfactant-fibrinogen mixtures containing antibiotics and growth factors which demonstrate sustained abnormalities in interfacial properties by PBS measurements. Factor XIIIa can be added to these samples to promote clot cross-linking. Clot stability at several concentrations of added factor XIIIa can be examined by assaying for clot dissolution in 8 M urea (plasma clot lysis time).

Both fibrin monomers and fibrinogen should cause significant alterations in surface film behavior (normalized b* values <0.2) at protein:phospholipid ratios >4). Moreover, the addition of thrombin, antibiotics, or growth factors should not markedly alter the ability of fibrin compounds to inhibit surfactant function at the concentrations required for these reagents to function in vivo. If these additives do markedly alter the biophysics of the interaction between surfactant and fibrinogen/fibrin, alternative reagents (or alternative reagent concentrations), can readily be considered.

A stable long term state of atelectasis with scarring within the targeted region is necessary to prevent subsequent partial or complete re-expansion following BLVR. This state can be achieved by using a biopolymer that promotes ingrowth of fibroblasts from adjacent regions within the lung and causes deposition of extracellular matrix (ECM) components. The procedures described below can be used to examine the ability of fibrin polymers containing varying concentrations of growth factors to stimulate fibroblast ingrowth. More specifically, they can be used to examine the ability of polymers with varying concentrations of growth factors to promote both initial cell attachment and subsequent growth.

Cell culture plates are coated with a mixture of fibrinogen, antibiotics, FGF (both with and without TGFβ) and the mixture is polymerized by addition of a small amount of thrombin. The plates are then washed with sterile Eagle's minimal essential medium to remove excess reagents and thrombin, and sterilized by overnight exposure to ultraviolet irradiation. Six types of plates are examined initially: the first and second are coated with fibrin polymer, antibiotics, and FGF at either a low or high concentration; the third and fourth are coated with fibrin polymer, antibiotics, and TGFβ at either low or high concentration; and the fifth and six are coated in similar fashion but contain both growth factors at either low or high concentrations.

Strain IMR-90 (human diploid fibroblasts available from the American Type Culture Collection, Manassas, Va.) are cultured in minimal essential tissue culture medium containing 10% fetal calf serum. Cells are brought to 80% confluence following initial plating, then harvested and passed twice in serum free media (MCDB-104, Gibco 82-5006EA, Grand Island, N.Y.). Established cultures are then sub-cultured onto coated 6-well plates at an initial density of $10^4$ cells/ml. Attachment efficiency (AE) for each coating mixture is assessed at 4 hours following plating by removing excess media, rinsing the wells in culture free media, and fixing each well with 70% histologic grade ethanol (Fisher Scientific, Pittsburgh, Pa.). Wells are stained with Geimsa, and the average number of cells attached per high power field (hpf) is determined by light microscopy. Twenty fields per well will be assessed in a blind study. Six wells per coating will be averaged to determine final counts, and the results will be compared to those of control samples plated on tissue culture plastic. Attachment efficiency will be expressed as an index (AEI) equal to the ratio of the number cells/hpf in experimental samples to the number of cells/hpf in control samples. Cell growth on each of the six biopolymer mixtures is assessed by determining the total number of cells present at 48 hours following plating. Cell growth is expressed in terms of a growth efficiency index (GEI) equal to the total number of cells at 48 hours for each sample normalized to the total number of cells at 48 hours of growth on tissue culture plastic. Cells are harvested and counted by removing the media from each well, and rinsing the well with calcium/magnesium free Hank's solution. The media will be saved for cell re-suspension. One ml of 0.2% trypsin solution is added to each well, and the cells are incubated for 2 minutes. Trypsin is then removed, and the adherent cells washed from the plate using the previously harvested media, which acts to inhibit further trypsin activity. The extent of residual cell adhesion is assessed by direct visualization using an inverted microscope. Residual adherent cells are removed by a second trypsin wash and total cell counts are obtained using a hemocytometer.

Cell attachment to a fibrin polymer should be equivalent to, or better than, that observed on tissue culture plastic. If cell attachment is poor using fibrin alone, the fibrinogen will be mixed with 3-5% fibronectin and polymerized. Fibronectin has fibrin binding sites at both its amino and carboxyl termini, with a central cell binding domain which is recognized by most adherent cells expressing β1 integrins. Addition of fibrinogen should result in improved cell adhesion.

GEI should also be increased in preparations containing bFGF at low and high concentrations, but may be decreased in preparations containing TGFβ because of the suppressant effects of TGFβ on cell proliferation. However, it should be possible to overcome any suppressant effects observed using TGFβ by using a combination of bFGF and TGFβ. This combination has the potential to promote both cellular ingrowth and increase collagen and fibronectin deposition with scar formation. If bFGF is not able to overcome the anti-proliferative effects of TGFβ, platelet derived growth factor (PDGF) may be used.

Example 4

A Sheep Model for Emphysema

Work in live animals can help establish the effectiveness, safety, and durability of BLUR. The sheep model of emphysema described here displays many of the physiological, histological, and radiographic features of emphysema. In preliminary studies, six adult ewes (weighing 27-41 kg) were treated with inhaled nebulized Papain, a commercially available mixture of elastase and collagenase, administered via a muzzle-mask using two high flow nebulizer systems connected in parallel. The system generates particles 1-5 microns in diameter. Each animal received 7,000 units of enzyme in saline over a 90 minute period at 0.3 ml/min. Approximately 30-40% of the total dose administered in this fashion was deposited at the alveolar level. One animal, which received saline according to a similar protocol, served as control.

All animals underwent detailed measurements of lung function before, and at monthly intervals after, inhalation treatments. The post-treatment assessment was continued for 3 months. Recordings were made following administration of anesthesia during controlled ventilation. Transpulmonary pressure was recorded using a pressure transducer. which recorded the pressure difference between the airway opening and the intrathoracic pressure measured using an esophageal balloon. Flow at the mouth was measured using a pneumotachograph attached to the proximal end of the endotracheal tube. Measurements of lung resistance, static lung compliance, and dynamic lung compliance were performed. After 3 months, all animals were sacrificed, and lung sections were prepared for histopathological evaluation.

Figure 5A:
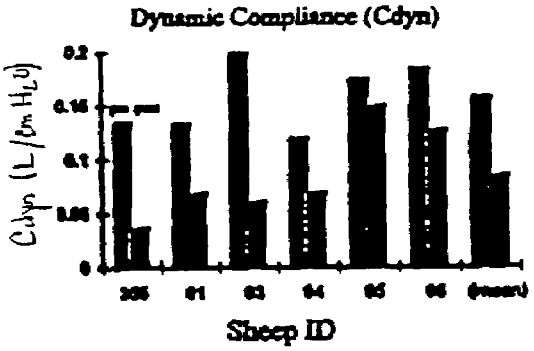
FIGS. 5*a* and 5*b* are bar graphs depicting dynamic (FIG. 5*a*) and quasi-static (FIG. 5*b*) compliance 3 months after sheep were exposed to Papain. n=6.
Figure 5B:
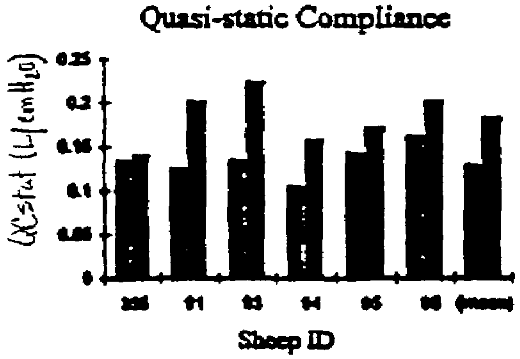

The results of static and dynamic lung compliance measured prior to exposure to Papain and at 3 months following Papain treatment, are summarized in FIGS. 5*a* and 5*b*. Static lung compliance increased significantly from 0.13±0.02 to 0.18±0.03 L/cm $H_2O$ (p=0.012, n=6), indicating disease heterogeneity and gas trapping.

Figure 6A:
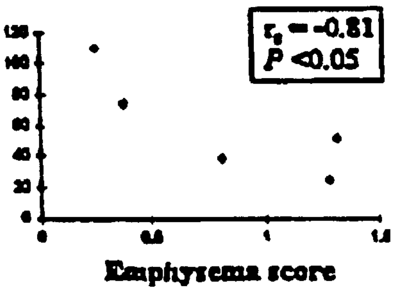
FIGS. 6*a* and 6*b* are graphs plotting the relationship between physiology (Cdyn, as a % baseline, is shown in FIG. 6*a* and $R_L$, also as a % baseline, is shown in FIG. 6*b*) and emphysema severity score.
Figure 6B:
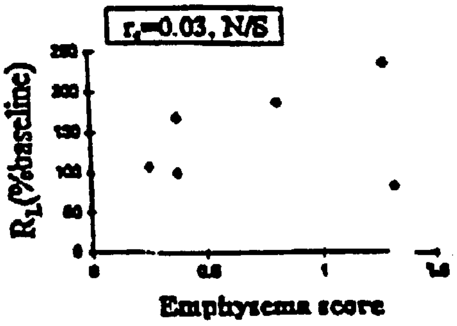

Physiological changes correlated with a semi-quantitative assessment of emphysema were also assessed histologically. In a blind study, eight sections (one per lobe) from each animal were scored as follows: 0=no emphysema; 1=mild emphysema; 2=moderate emphysema; 3=severe emphysema. A total score was determined as the average from eight sections prepared from each animal. Total lung resistance tended to increase with emphysema severity score, although this correlation was not statistically significant due to the presence of one outlier, and the small number of animals studied. Dynamic compliance did correlate inversely with emphysema severity score in a significant fashion (FIGS. 6*a* and 6*b*).

Example 5

In Vivo Application of BLVR

Induction of emphysema in sheep, as described above, provides an excellent model in which to test both the safety and efficacy of BLVR. In the studies described below, eight sheep having emphysema were analyzed; four did not receive treatment and four were treated with BLVR. Measurements were performed: (1) at baseline prior to papain exposure; (2) eight weeks following papain exposure (at which time all animals had developed emphysema) and; (3) six weeks following either sham bronchoscopy without lung volume reduction (control) or BLVR performed with a fibrinogen-based composition (experimental). More specifically, the experimental animals were treated with a fibrinogen-based solution containing 5% fibrinogen, which was subsequently polymerized with 1000 units of thrombin in a 5 mM calcium solution.

All animals demonstrated physiological evidence of emphysema with increased lung resistance, increased dynamic elastance, increased total lung volumes, and changes in static pressure volume relationships consistent with mild to moderate emphysema. Thus, papain therapy administered via nebulizer, as described above, caused emphysema.

Figure 7:
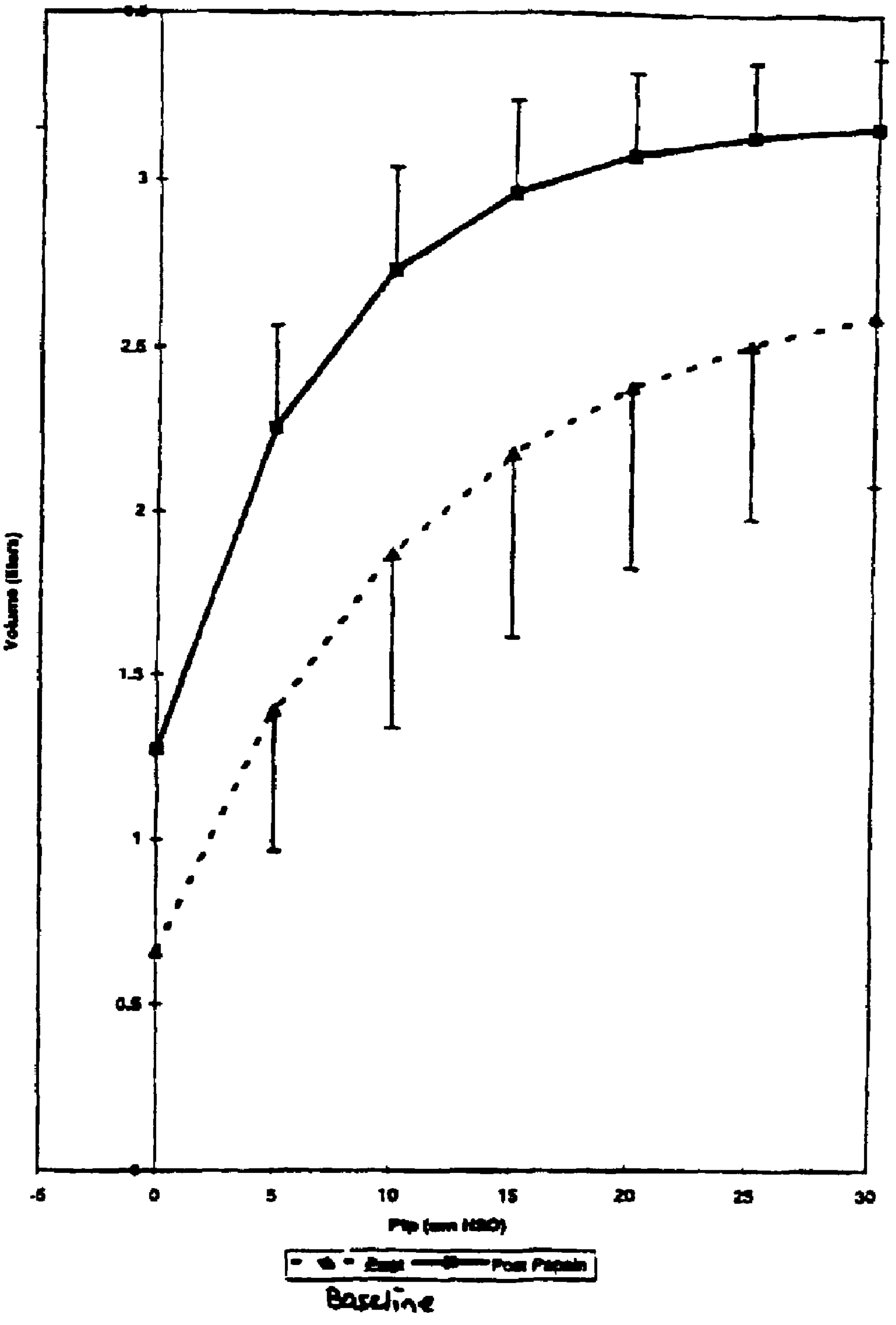
FIG. 7 is a graph illustrating static lung compliance (volume in liters vs. Ptp in cm $H_2O$) at baseline (i.e., pre-treatment) and at eight weeks following papain therapy in sheep.

After six weeks, animals with papain-induced emphysema that did not receive any therapy had persistent increases in lung resistance (125% at normal breathing frequency compared to pre-treatment baseline) and dynamic elastance (31% at normal breathing frequency compared to pre-treatment baseline). Static lung behavior remained markedly abnormal compared to baseline, with lung volumes increased 33% compared to pre-treatment baseline. These results are summarized below in Table 3 and shown in FIG. 7.

TABLE 3

| Treatment | RL (cm $H_2O$/L/sec) at f = 10 b/min | EL (CM $H_2O$/L) at f = 10 b/min | Raw (cm $H_2O$/L/sec) |
|---|---|---|---|
| Baseline (n = 8) | 1.71 ± 0.36 | 10.85 ± 2.78 | 0.50 ± 0.23 |
| Post-Papain (n = 8) | 3.03 ± 0.47 | 13.51 ± 3.81 | 1.17 ± 0.39 |
| Statistical Significance | p = 0.041 | p = 0.20 | p = 0.029 |

In contrast, after six weeks, animals treated with BLVR experienced a significant reduction in airway resistance, in total lung resistance at normal breathing frequency, in total lung capacity, and in resting lung volumes. These results, which are summarized in Table 4, indicate a significant improvement in lung physiology compared to pre-volume reduction, and a significant improvement relative to untreated animals.

TABLE 4

| Experimental Group | Raw (cm $H_2O$/L/sec) | RL (cm $H_2O$/L/sec) at f = 10 b/min | FRC (liters) resting lung volume | TLC (liters) maximum lung volume |
|---|---|---|---|---|
| Pre-treatment volume reduction | 0.61 ± 0.31 | 3.47 ± 1.14 | 1.27 ± .031 | 3.31 ± 0.62 |
| Post-treatment volume reduction | 0.82 ± 0.31 | 1.85 ± 0.57 | 0.97 ± 0.21 | 2.85 ± 0.71 |
| Control following sham treatment | 1.14 ± 1.22 | 3.21 ± 0.97 | 0.80 ± 0.31 | 2.76 ± 0.49 |

Moreover, all animals treated by BLVR tolerated the procedure well. They were able to breathe without ventilator support within one hour of completion of the procedure, and all animals were eating and drinking normally within 24 hours. One of four animals developed a fever, which lasted two days, and was easily managed with five days of intramuscular antibiotic therapy. No other complications were noted. Thus, the physiological response to BLVR was very positive.

Example 6

The Effect of ECM Components on the Properties of Fibrin Gels

The effects of CS, HA, Fn, and PLL on: the mechanical properties of solutions that promote tissue collapse or tissue adhesion; the rate at which solutions polymerize; and the ability of such solutions to support fibroblast growth have been studied. To characterize the mechanical properties, circular gels were formed in 12-well cell culture dishes, gel strips (4×4×10 mm) were excised using a razor blade, and the elastic (H) and dissipative moduli (G) of the strips was measured as they were stretched using a servo-controlled computerized length actuator system and coupled force transducer device. In addition, the stress at yield ($Y_s$) for each preparation was measured to assess strength and durability under conditions of uniaxial stretching, and fatigue was tested with a solution containing CS and PLL (see below). This solution exhibited desirable mechanical properties. Polymerization rates ($k_P$) were estimated using a stop watch and defined as the inverse of the amount of time required to inhibit the rotation of a small, magnetic mixing bar rotating within the solution at 4π radians/second at the time polymerization was initiated. Cell culture studies were performed by growing fibroblasts (WS-1 transformed human fibroblast cell line) on pre-formed gels, as well as within gels polymerized after mixing fibrinogen reagents with fresh cell suspensions. To assess cell proliferation, the number of cells present per 10 high-power fields was counted after plating at a uniform cell concentration and the MTT cell proliferation assay was performed.

All ECM components tested were soluble in fibrinogen dissolved in buffered saline at pH 7.4, although the solution required warming to dissolve HA. Fibrin gels were prepared using aqueous bovine fibrinogen (fraction VII, Sigma Chemical Co., St. Louis Mo.) at a final concentration of 3%, 2.5 mM $CaCl_2$ and 0.025 mM dipalmitoylphosphatidylcholine (DPPC). Calcium and DPPC concentrations were determined in preliminary work performed to optimize polymerization rates of fibrinogen. Polymerization was effected using thrombin at 100 units/ml of fibrinogen solution (3.3 units of thrombin/mg fibrinogen). CS, PLL, and HA were tested at 0.01, 0.1, and 0.3% (relative to fibrinogen) by weight. Fn was tested at 0.001 and 0.01%. Results were compared to fibrin gels without additives, and with commercially available fibrin glue marketed as a tissue sealant (Baxter Pharmaceutical, Tisseal™). Samples were tested within 30 minutes of gel formation, and at 24, 48, and 168 hours after gel formation while maintained in aqueous solution at room temperature.

The effects on mechanical properties of adding extracellular matrix components to fibrin gels are summarized in FIGS. 8*a* and 8*b*. The addition of low molecular weight HA decreased $k_P$ (slowed polymerization) significantly, while CS, PLL, and Fn had no effect on polymerization rates. The addition of CS (at 0.1 and 0.3%) and PLL (0.05%) increased gel elastance (H) about 55% and 50% respectively, while addition of HA had no effect. Changes in dissipative behavior (G) of the gel strips paralleled elastic behavior closely such that the ratio of dissipative to elastic moduli, eta ($\eta$=G/H) remained relatively constant for all preparations (range of $\eta$0.1 to 0.15 for all samples). Gel yield stress was markedly improved by addition of 0.05% PLL, but was not significantly affected by addition of other components.

Polymerization rates and mechanical properties of fibrin gels containing single additives were used to develop gel combinations that contained agents theorized to promote macrophage and fibroblast chemotaxis and collagen deposition. A final gel combination containing 0.1% CS, 0.1% PLL, 0.1% HA, and 0.01% Fn polymerized rapidly, retained its mechanical properties after one week in saline solution, resisted rupture during repeated stretching and distortion. Moreover, these properties were bestowed by agents that modulate the behavior of cells in the area of tissue collapse.

Figure 9:
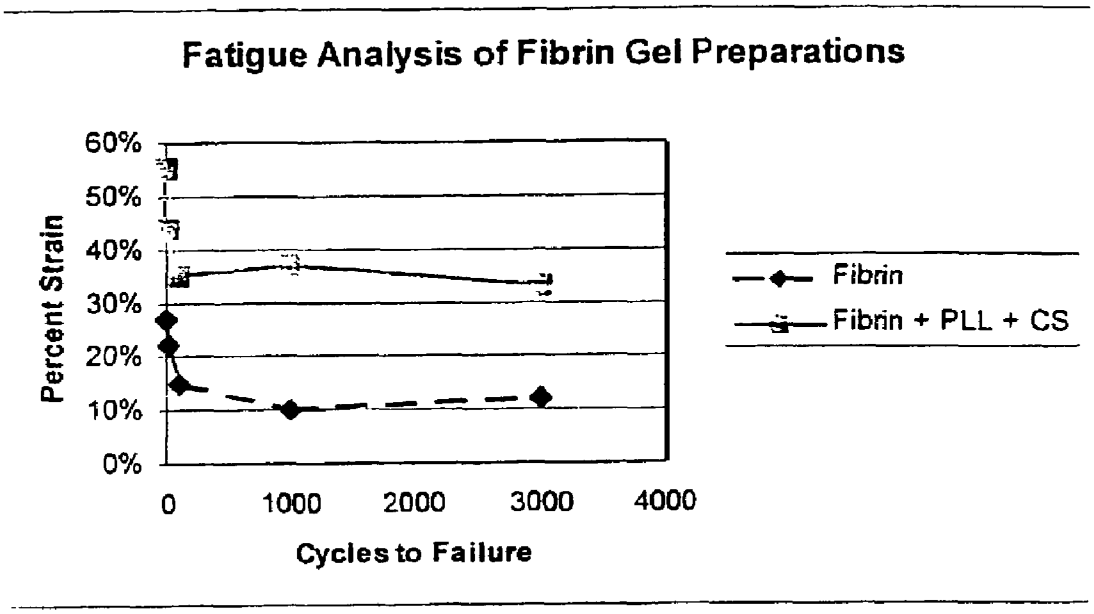
FIG. 9 is a line graph plotting percent strain v. cycles to failure for gel strips composed of fibrin alone or fibrin+PLL+CS.

FIG. 9 summarizes tests for fatigue in which a standard fibrin gel was compared with a fibrin gel containing 0.05% PLL and 0.1% CS. The modified fibrin gel demonstrates a higher yield stress and a greater ability to resist fatigue related failure when tested during repeated sinusoidal cycling over a range of strain amplitudes. As shown in FIG. 9, gel strips composed of fibrin alone demonstrated ductile rupture at much lower percentage strains than a fibrin solution containing PLL and CS. The "infinite" life of the modified fibrin glue preparation, represented by the percentage strain below which failure does not occur, is significantly greater (32% strain) than that of standard fibrin glue (10% strain).

Figure 10A:
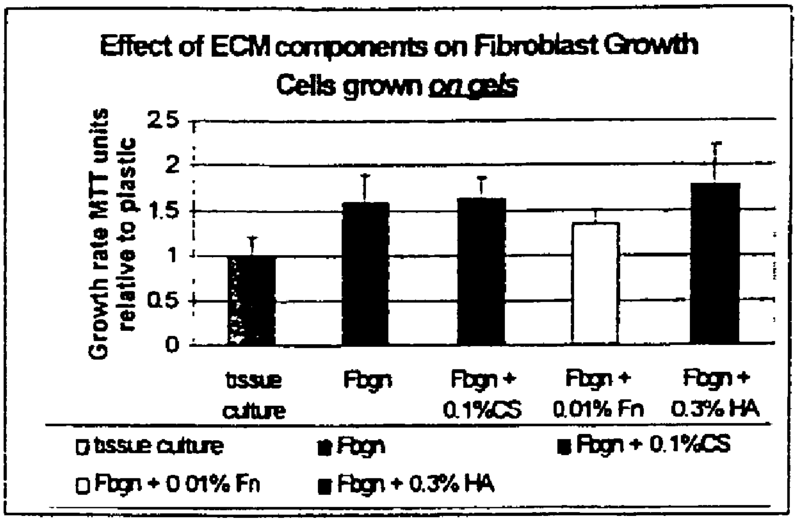
FIGS. 10*a* and 10*b* are bar graphs of human fibroblast proliferation on fibrin gels containing ECM components.
Figure 10B:
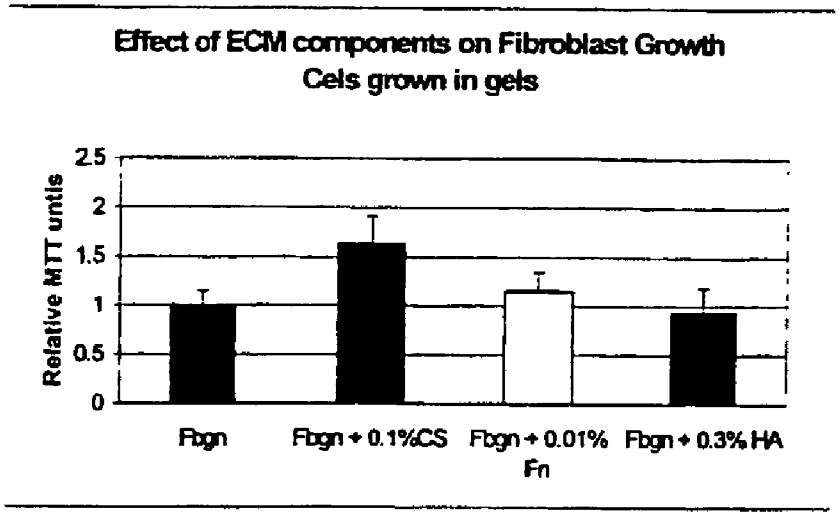

Fibrin gel preparations were also tested for their ability to support fibroblast growth not only on their surface, but also within the polymer mixture at the time of polymerization. Cell proliferation was assayed by counting the number of cells in 10 high-power fields and by performing an MIT (3, 4, 5, dimethyl-thiazol-2-yl-2,5, diphenyltetrazolium bromide) dye proliferation assay. Assays were performed 96 hours after culture initiation at an initial plating density of $2\times10^6$ cells/well. Assays were performed using WS-1 human fibroblasts, as well as 3T3 murine fibroblasts obtained from the American Type Cell Culture Collection (ATCC; Manassas, Va.). Counts were normalized to those measured on standard tissue culture plastic. The results obtained by the two assays (cell counting and MTT) were similar (FIGS. 10*a* and 10*b*). Compared to growth on tissue culture plastic, cell proliferation was accelerated for both WS-1 and 3T3 grown when grown on top of fibrin gels. CS (0.1% and 0.3%), Fn (0.001 and 0.01%), and HA (0.1 and 0.3%) had no additional effect on cell growth rates above that observed for fibrin gels alone (FIG. 10*a*, left panel). Conversely, none of these additives had an adverse effect on cell proliferation. Studies in gels (FIG. 10*b*) demonstrated that CS (0.1%) and Fn (0.01%) both promote fibroblast proliferation relative to fibrin gels without additives and relative to those containing HA. The combination of CS and Fn had the most dramatic effect. Histomicrographs of WS-1 fibroblasts in gels demonstrate that CS and Fn together promote fibroblast proliferation and organotypic organization. Thus, addition of this combination of ECM components promotes both fibroblast proliferation and cellular organization into linear and cross-linked arrangements suggestive of organotypic growth patterns. Therefore, fibrin gels containing CS (0.1%) and Fn (0.01%) promote fibroblast proliferation and organotypic organization and growth patterns. PLL significantly improves the mechanical properties of fibrin gels by increasing elasticity and resistance to fracture. Because HA slows polymerization rates without clearly improving the mechanical properties of fibrin-based gels or promoting macrophage chemotaxis in vitro, HA may be a better additive for the "anti-surfactant" washout solution than the fibrin glue itself. In vivo studies presented below support this conclusion.

Example 7

"Living" Bio-Polymers

The studies described above, which demonstrate that lung fibroblasts can be cultured within modified fibrin gels, indicate that gels containing cells harvested from a patient's target tissue, another of the patient's tissues, a different human (e.g. a relative or an organ donor), or a fetus (e.g., fetal lung tissue) can be used to achieve targeted lung volume reduction. Thus, for a human patient with emphysema, fibroblasts harvested from a skin biopsy, exposed in vitro to specific growth factors, and administered to the lung using the fibrin-based glues of the invention (which may or may not contain the agents described above, such as components of the ECM) could be used to effectively achieve tissue volume reduction and promote focal scarring. The type of cells used may vary depending on the objective to be achieved. For example, a combination of the patient's own lung cells and stem cells (perhaps obtained from fetal tissue) could be used to reduce lung volume and promote the growth or re-growth of pulmonary tissues.

Example 8

In Vivo Studies Using Fibrin-Based Solutions Containing

Many of the solutions described herein have been tested for safety, biocompatibility, and utility in lung volume reduction in intact animals. Safety and biocompatibility were tested in sheep that did not have pulmonary disease (i.e., the sheep had not been exposed to papain, which causes a condition like emphysema). The animal's baseline lung function (including lung volumes and static pressure volume inflation curves) was measured at time zero (i.e., prior to treatment) and during the weeks following treatment. All animals were anesthetized with ketamine and Valium, and were maintained with intravenous Propofol. An esophageal balloon was placed to measure intrathoracic pressure. Animals were maintained on mechanical ventilator support through the measurement periods. Between tests, animals were returned to their cages and allowed to eat and drink without restriction.

Figure 11:
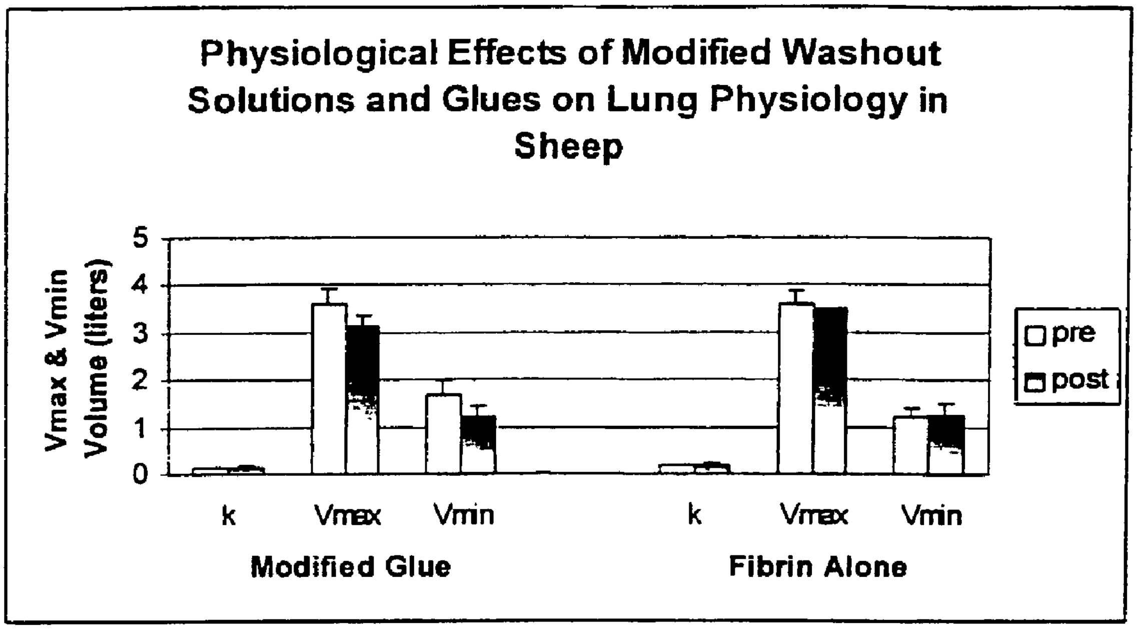
FIG. 11 is a bar graph depicting the effects of modified washout solutions and glues on lung physiology in sheep.

The whole animal experiments described above were modified as follows. Previously, 50 mls of fibrin glue was used to seal each subsegmental target region, but in the present study only 10 mls of fibrin solution was used in each region (the focus being on biology rather than biomechanics and the aim being to limit abscess formation). Saline washout combined with unmodified fibrin glue (n=2) was compared to a modified washout solution (10% ethanol, 0.5% fibrinogen, 0.3% low molecular weight hyaluronic acid, and 0.01% fibronectin) combined with a fibrin glue containing 0.1% CS, 0.1% PLL, and 0.05% HA (n=4). The results are summarized in FIG. 11, where the relationship between pressure and volume is expressed according to the exponential fit equation of Salazaar and Knowles:

$$V(P)=V_{max}-(V_{max}-V_{min})e^{-kP}$$

where $V_{max}$=total lung capacity at maximum distending pressure; $V_{min}$=residual lung volume at zero distending pressure; and k is the shape factor describing the shape of the exponential relationship between pressure and volume. Comparisons of $V_{max}$, $V_{min}$, and k pre- to post-treatment for saline+fibrin glue treated animals, and modified washout+modified glue treated animals are shown. In saline+fibrin glue treated animals, no differences were noted in maximum lung volumes ($V_{max}$=3.6±0.28 L pre to 3.49±0.62 L post), minimum lung volumes ($V_{min}$=1.22±0.18 L pre- to 1.28±0.21 L post), or shape factor (k=0.19±0.02 pre to 0.19±0.05 post). In animals treated with washout solutions and glue as described above to promote fibroblast growth, chemotaxis, and collagen deposition decreases in $V_{max}$ (3.61±0.31 L pre- to 3.15±0.22 L post; p=0.11 by paired t test) and $V_{min}$ (1.69±0.31 L pre- to 1.22±0.23 L post-; p=0.007) were noted, but k (0.14±0.02 pre- to 0.15±0.04 post-) remained unchanged.

Figure 12A:
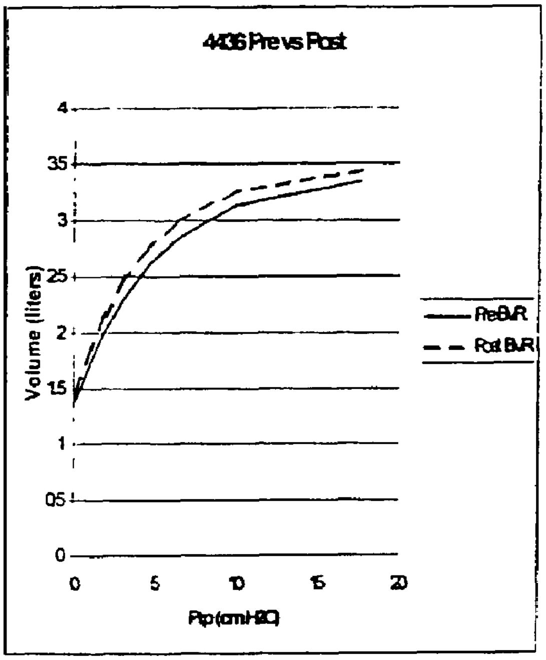
FIGS. 12*a* and 12*b* are line graphs showing a quasi-static pressure volume relationships for a sheep treated with 4×10 ml subsegmental washout plus fibrin glue (the results after two weeks are shown in FIG. 12*a*) and a sheep treated with washout solution containing ECM components (FIG. 12*b*).
Figure 12B:
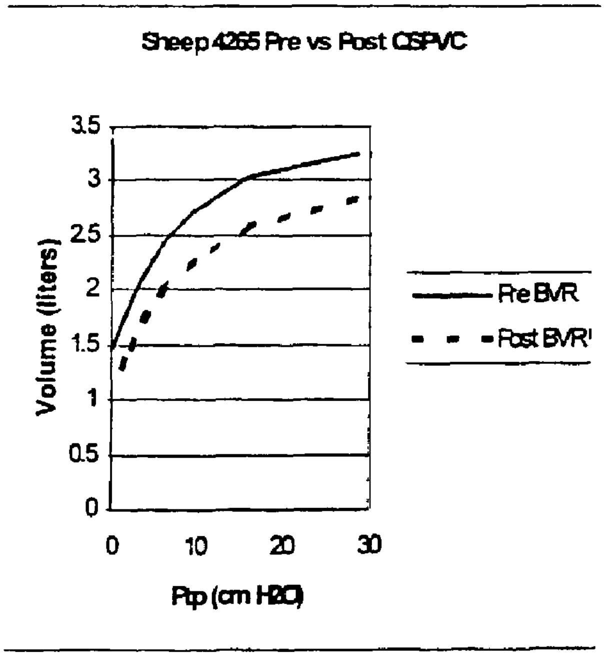

Examples of individual quasi-static pressure volume relationships from a saline washout+fibrin animal and a modified washout+modified glue animal are shown in FIGS. 12*a* and 12*b*. Animals treated with saline+fibrin glue alone demonstrated no decrease in lung volumes as a result of therapy. By contrast, animals treated with modified washout+glue demonstrated a marked reduction in both $V_{max}$ and $V_{min}$, and a down and rightward shift in the entire pressure volume relationship indicating an overall decrease in lung volume.

In contrast to the study in which all animals treated with 50 mls of fibrin glue required oxygen post procedure, and 2 of 4 animals required antibiotics for fever, none of the animals in either the saline or the modified washout+glue treatment groups required oxygen or antibiotics. Furthermore, necropsy studies on treated lungs showed no evidence of abscess formation.

These data indicate that the modified surfactant washout solutions and fibrin glues described herein can be used to achieve safe and effective volume reduction therapy. They support the studies showing that effective tissue reduction therapy in the lung can be achieved without surgery using biocompatible glues and also establish the viability of approaches using agents that modulate specific aspects of the biology of lung fibroblasts, alveolar cells, macrophages, and endothelial cells.

Example 9

Modified Fibrin-Based Glues can Seal Air Leaks in the Lung

The studies that follow demonstrate that the solutions of the invention can effectively seal air leaks in the lung. The mechanical properties of the solutions described herein are superior to other fibrin-based preparations and allow the novel solutions of the present invention to resist fracture during repeated distortion (FIG. 9). Patients undergoing chest surgery will benefit from the use of modified fibrin-based glues for sealing air leaks. Chest surgery is common. More than a quarter of a million patients undergo this type of surgery every year due to, for example, resection of lung nodules and cancers, resection of tissue for confirming a diagnosis of an unknown lung disease, and resection of chronic infections refractory to conventional medical therapies. Because lung tissue is delicate, leaks resulting from tissue tearing are common following surgery. The reported incidence is 25-40%. Tears in the lung require long periods to heal, especially in patients with severe underlying lung disease, and prolonged air leaks contribute significantly to morbidity and mortality.

The application of the fibrin glues described herein, particularly those modified to include components of the ECM, can be applied either as primary therapy for preventing leaks in general thoracic surgery cases, or secondarily to seal existing or persisting leaks, whether they have arisen from prior surgery or intrinsic disease The leaking region can be identified with a dual balloon finder-injection catheter system (FIGS. 14*a* and 14*b*). Once the region has been identified and isolated, solutions can be injected distally to effect sealing. These solutions can be identical to those used for effecting volume reduction since the same polymerization, biocompatibility, mechanical, and biological characteristics are desirable in both instances.

Studies have been conducted in isolated calf lungs using the dual balloon finder-injector and modified fibrin glues to identify, localize, and seal pleural leaks. As described above and shown in FIGS. 8*a*, 8*b*, and 9, the addition of biocompatible polymers within fibrin matrices markedly strengthens the resulting gel-polymer, and reduces gel fracture during cyclic fatigue (which simulating airway-related stress). These preparations are significantly stronger and more durable in vitro than conventional fibrin glues. The modifications required to increase the mechanical strength of the glues did not adversely affect the polymerization rates of the gels. Thus, accurate and timely delivery is preserved.

In three separate isolated bovine lung experiments, these glues completely sealed 13 of 17 air leaks following administration through the finder-injector catheter system. The leaks were sealed up to distending pressures of 50 cm $H_2O$. Glue administration reduced the extent of leakage in all cases, as assessed by a decrease in flow through the leak at a fixed distending pressure (of 50 cm $H_2O$).

Other Embodiments

While the compositions and methods of the present invention are particularly suitable for use in humans, they can be used generally to treat any mammal (e.g., farm animals such as horses, cows, and pigs and domesticated animals such as dogs and cats).

In addition, the compositions described above can be usefully applied to a variety of tissues other than the lung. For example, they can be applied to seal leaks of cerebrospinal fluid; to seal anastomoses of native and prosthetic vascular grafts (including those associated with the implantation of prosthetic valves such as mitral valves); in diagnostic or interventional procedures or endoscopic or orthopedic procedures involving the intentional or accidental puncture of a vessel wall; in plastic surgery; and in highly vascular cut tissue (e.g., the kidneys, liver, and spleen). The compositions described above can also be applied to accelerate healing in diabetics and to treat septic wounds of longstanding resistance to standard approaches, including antibiotic-resistant bacterial infections.

What is claimed is:

1. A method for reducing lung volume in a patient, the method comprising:

(a) advancing a bronchoscope into the vicinity of a diseased alveolar region of a lung targeted for volume reduction in a patient; and (b) introducing material through the bronchoscope into the diseased alveolar region thereby reducing the volume of the diseased alveolar region; wherein said material induces collapse of the diseased alveolar region; said material promotes adhesion between one collapsed diseased alveolar region of the lung and another; and said material promotes fibrosis in or around the collapsed diseased alveolar region of the lung; wherein the material comprises fibrin or fibrinogen.

2. The method of claim 1, wherein the material comprises fibrin or fibrinogen.

3. The method of claim 2, wherein the material further comprises a polypeptide growth factor.

4. The method of claim 3, wherein the polypeptide growth factor is a fibroblast growth factor or a transforming growth factor beta-like (TGFβ-like) polypeptide.

5. The method of claim 2, wherein the material further comprises a component of the extracellular matrix (ECM) or an ECM-like substance.

6. The method of claim 5, wherein the component of the ECM comprises hyaluronic acid (HA), chrondroitin sulfate (CS), or fibronectin (Fn).

7. The method of claim 5, wherein the ECM-like substance comprises poly-L-lysine or a peptide consisting of proline and hydroxyproline.

8. The method of claim 2, wherein the material further comprises an agent that causes vasoconstriction.

9. The method of claim 8, wherein the agent that causes vasoconstriction is an endothelin, epinephrine, or norepinephrine.

10. The method of claim 2, wherein the material further comprises a proapoptotic agent.

11. The method of claim 10, wherein the pro-apoptotic agent is sphingomyelin, Bax, Bid, Bik, Bad, Bim, caspase-3, caspase-8, caspase-9, or annexin V.

12. The method of claim 1, further comprising blocking air flow into or out of the region.

13. A method for performing lung volume reduction, the method comprising introducing material through an airway of a patient into a diseased alveolar region of the patient's lung to:

(a) collapse the diseased alveolar region;

(b) adhere one portion of the collapsed diseased alveolar region to another; and (c) promoting fibrosis in or around the collapsed diseased alveolar region of the lung; wherein the method is performed using a bronchoscope; wherein collapse of the diseased alveolar region of the lung is achieved by administering a substance that increases the surface tension of fluids lining the alveoli in the targeted region; wherein the substance is fibrinogen or fibrin.

14. The method of claim 13, wherein the substance is fibrinogen.

15. The method of claim 13, wherein the substance is fibrin.

16. The method of claim 13, further comprising blocking air flow into or out of the targeted region.

17. The method of claim 13, wherein adhering one portion of the collapsed region to another is achieved by administering a solution comprising fibrinogen and a fibrinogen activator.

18. The method of claim 17, wherein the fibrinogen activator is thrombin.

19. The method of claim 18, wherein the fibrinogen comprises 3-12% fibrinogen.

20. The method of claim 19, wherein the fibrinogen comprises approximately 10% fibrinogen.

21. The method of claim 17, further comprising administration of factor XIIIa transglutaminase.

22. The method of claim 13, wherein adhering one portion of the collapsed region to another is achieved by administering fibrin.

23. The method of claim 22, further comprising administration of factor XIIIa transglutaminase.

24. The method of claim 13, wherein promoting fibrosis in or around the collapsed region of the lung is achieved by administering a polypeptide growth factor.

25. The method of claim 24, wherein the polypeptide growth factor is a fibroblast growth factor (FGF).

26. The method of claim 25, wherein the FGF is basic fibroblast growth factor (bFGF).

27. The method of claim 24, wherein the polypeptide growth factor is transforming growth factor-beta (TGF-β).

28. The method of claim 13, further comprising reducing the risk of infection by administration of an antibiotic.

29. The method of claim 28, wherein the antibiotic is administered together with fibrinogen, fibrin, or a fibrinogen activator.

30. The method of claim 13, further comprising, prior to collapsing a region of the lung, inflating the region with absorbable gas.

31. The method of claim 30, wherein the absorbable gas is at least 90% oxygen.

32. A method for reducing lung volume in a patient, the method comprising:

introducing a material into a diseased alveolar region of a patient's lung, thereby collapsing the diseased alveolar region and reducing the volume of the lung; wherein the material comprises an anti-surfactant, or an adhesive, or a combination thereof; reducing airflow into and out of the diseased alveolar region; wherein the material is introduced through a trachea or a smaller airway of a patient.

33. The method of claim 32, blocking air flow into and out of the target region using a balloon catheter or other method or device.

34. The method of claim 32, comprising occluding a trachea, bronchus, bronchiole or other airway of the lung.

35. The method of claim 32, further comprising occluding the diseased alveolar region and filling the occluded region with an absorbable gas prior to collapsing the region.

36. The method of claim 32, wherein the material comprises one or more agents selected from the group consisting of an agent that increases the surface tension of fluids lining the alveoli, an agent that adheres one portion of a tissue to another, an agent that promotes chemotaxis, an agent that promotes collagen deposition, an agent that causes inflammation, an ECM-like agent, a pro-fibrotic agent, an agent that causes vasoconstriction, an agent that modulates endothelial cell response, a polymerizing agent, a pro-apoptotic agent, an agent that promotes fibrosis or scarring, other agents that act mechanically and/or biologically, and other biocompatible reagents.

* * * * *